(12) United States Patent
Van Den Berg

(10) Patent No.: US 10,577,611 B2
(45) Date of Patent: Mar. 3, 2020

(54) MULTI-SPECIES POLYNUCLEOTIDE CONTROL SEQUENCES

(71) Applicant: DSM IP ASSETS B.V., Heerlen (NL)

(72) Inventor: Marco Alexander Van Den Berg, Poeldijk (NL)

(73) Assignee: Centrient Pharmaceuticals Netherlands, B.V. (NL)

( * ) Notice: Subject to any disclaimer, the term of this patent is extended or adjusted under 35 U.S.C. 154(b) by 336 days.

(21) Appl. No.: 14/249,533

(22) Filed: Apr. 10, 2014

(65) Prior Publication Data

US 2015/0232860 A1 Aug. 20, 2015

Related U.S. Application Data

(63) Continuation of application No. 12/997,330, filed as application No. PCT/EP2009/057225 on Jun. 11, 2009, now abandoned.

(30) Foreign Application Priority Data

Jun. 11, 2008 (EP) ..................................... 08158028

(51) Int. Cl.
| | |
|---|---|
| C12N 15/00 | (2006.01) |
| C07H 21/00 | (2006.01) |
| C12N 15/63 | (2006.01) |
| C12N 15/70 | (2006.01) |
| C12N 15/80 | (2006.01) |
| C12N 15/81 | (2006.01) |
| C12N 15/75 | (2006.01) |

(52) U.S. Cl.
CPC ............ *C12N 15/63* (2013.01); *C12N 15/70* (2013.01); *C12N 15/75* (2013.01); *C12N 15/80* (2013.01); *C12N 15/81* (2013.01)

(58) Field of Classification Search
CPC ..... C07H 21/00; C12N 15/00; A01K 2267/01
See application file for complete search history.

(56) References Cited

U.S. PATENT DOCUMENTS

2003/0124679 A1* 7/2003 Short ..................... C07H 15/24
435/76
2011/0165585 A1 7/2011 Van Den Berg

FOREIGN PATENT DOCUMENTS

EP 0 479 426 4/1992

OTHER PUBLICATIONS

International Search Report for PCT/EP2009/057225, dated Aug. 5, 2009.
Patek et al., "Function of Corynebacterium Glutamicum Promoters in *Escherichia coli*, Streptomyces Lividans, and Bacillus Subtilis", Journal of Biotechnology, Elsevier Science Publishers, Amsterdam, NL, vol. 104, Jan. 1, 2003, pp. 325-334, XP002323103.
Alvarez et al., "Characterization of Yeast DNA Sequences Capable of Directing Transcription in Streptomyces and *Escherichia coli*", FEMS Microbiology Letters, Amsterdam, NL, vol. 115, No. 2-3, Jan. 15, 1994, pp. 119-124, XP023716229.
Asturias et al, "A bifunctinal Streptomyces-*E. coli* promoter-probe vetor", FEMS Microbiology Letters 56:65 (1990). Abstract Only.
Azza et al, "Cloning of the wide spectrum amidase gene from *Brevibacterium* sp. R312 by genetic complementation. Overexpression in *Brevibacterium* sp. and *Escherichia coli*", FEMS Microbiology Letters 122:129 (1994).
Hamer et al, "Gene discovery and gene function assignment in filamentous fungi", PNAS 98:5110 (2001).
Pel et al, "Genome sequencing and analysis of the versatile cell factory Aspergillus niger CBS 513.88", Nature Biotechnology 25(2):221 (2007).

* cited by examiner

*Primary Examiner* — Ethan C Whisenant
(74) *Attorney, Agent, or Firm* — William D. Hare, Esq.; McNeely, Hare & War, LLP

(57) ABSTRACT

The present invention relates to polynucleotide sequences which enable a polynucleotide control sequence, such as a promoter, to direct expression in a wide range of industrially relevant species, both prokaryotes and eukaryotes. When the polynucleotide sequences of the invention are applied in combination with selection marker genes it is possible to perform selectable cloning in a laboratory host and use the same construct in the final host.

18 Claims, 8 Drawing Sheets

Figure 5:

Specification includes a Sequence Listing.

Fig. 1

A.
tgcatgttgcatcgggaaatcccaccacagggacagccaagcggccccgcgacttggcag
CATATG
tgggcaaactacgcccgattctggtgccaagaaccgagaagaatgagacagacccacgtt
gcactctaaccggatgctatcgacttacggtggctgaagattcaacacgctgcaacgaga
gccaaggtggtccggacattttctacgtgccggtttaccttggaacatcgccgtcgttga
gtgcacgttgcctactctctcgtggcttggctgggcccacgagcccgattgactcgacgg
tgttacttgggtatctatggcccgttttctggcacggtaatgataagtacttactagtc
ttcgagcgggggagtgttgctctgcccgagcatcaacgattggcctgatcgcaccgtctg
  GAATTC
caaatgccacggtgcggaccgactgaaatctcagaccaccaaagaccctccgacttcgag
ttacggttactaattttacactggctccagcggccccatccagtaagcatctgggctgca
agcgtataatgtctccaggttgtctcagcataaacaccccgccccgctcaggcacacag
                                  CAATTG
gaagagagctcaggtcgtttccattgcgtccatactcttcactcattgtcatctgcagga
gaacttcccctgtcccttttgccaagccctctcttcgtcgttgtccacgccttcaagtttt
caccattattttctagacaccATGgcttccacccc
         GTTAAC    atATCGATg

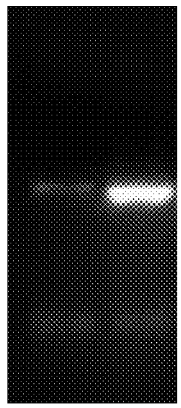
B. G L

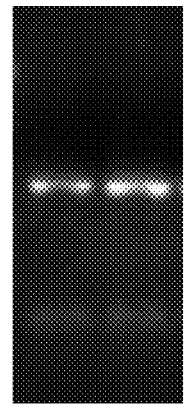
C. G L

Fig. 2.

A. ...ttgtcatctgcaggagaacttccctgtccccttgccaagccctctcttcgtgtgtccacgccttcaagtttcaccattattttctagaccatATG B. atccacgctgtgtaaaatttacaaaaaggtattgactttccctacaggggtgtgtaataatttaattacagctcgagaattaaaggaggtttcatATG C. ...cttcccatcccttattccttttgaaccttcagttcgagctttcccacttcatcgcagcttgactaacagctaccccgcttgagcagacatccatATG

Fig. 3.

A. .....atccacgctgtgtaaaatttacaaaaagtattgacttttccctacagggtgtgtaataattaattacagctcgagaattaaggagggtttcatATG B.
WT → ......agaacttccctgtccctttgccaagccctctctcgtcgttgtcaagccttcaccattatttctagacatATG
INS → ......agaaAActtccctgtccctttgccAAAagcccttTTGActtcgtcgttgtccacgccTATAAttcaagtttcaccattatttctGGAGGagaccatATG
EXC → ......agAaAacttccctgtccctttgaAcTagccctctcttcgtTgttAtAAtcgccttcaagtttcaccattattGGAGgagaccatATG C.
WT → ......attccttgaacctttcagttcgagctttcccacttcatcgcagcttgactaacagctaccccgcttgagcagacatccatATG
INS → ......attccttgAAAaacctttcAAAAgttcagTTGActttccactttcatcgcagcATAAttgactaacagctaccccgcttgagGagGacatccatATG
EXC → ......cttcccatccccttattcctAAAaaccctttTTGACTgagctttcccacttTGtcATaATtgactaacagctaccccgcttgagGagGcatccatATG Fig. 4
A.
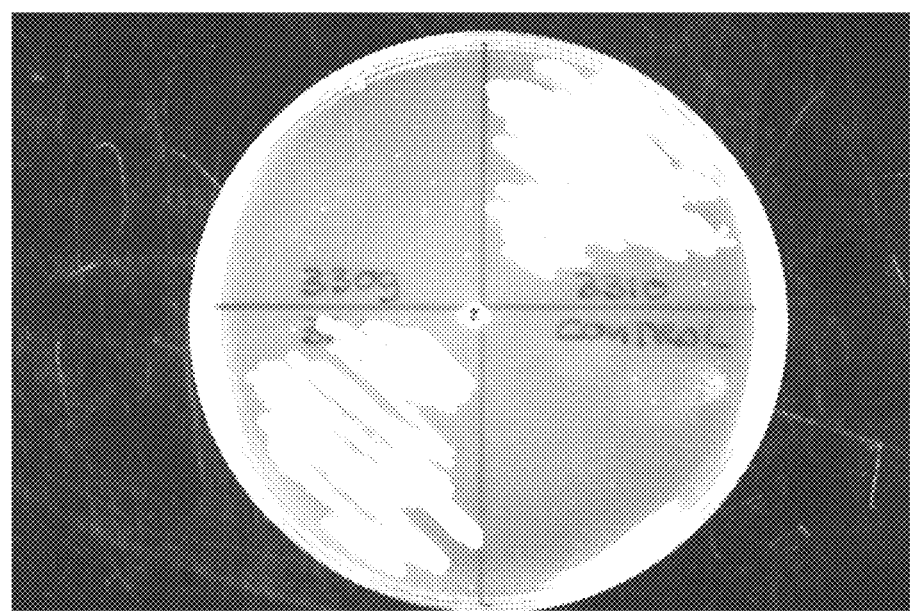
B.
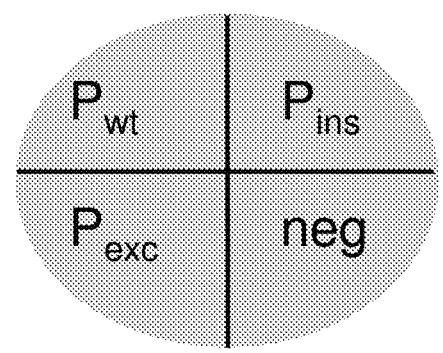

```
WT    →  ........ctcttggaaagtcttggaaattgactcttttttgcctcctttacaatctacccctttaatctttgcgactcgtttcttcaccATG
CD1   →  ........ctcttggaaagtcttggaaattgactcttttttgcctcctttacaatctacccctttaatctttgcgactcgtttcttcCATATG
CD2   →  ........ctcttggaaagtcttggaaattgactcttttttgcctcctttacAtttaatctacccAttaatctttgcgactGgAGGcttcCATATG
```

A.

B.

MULTI-SPECIES POLYNUCLEOTIDE CONTROL SEQUENCES

This application is a continuation of application Ser. No. 12/997,330 (abandoned), filed Dec. 10, 2010 (published as US 2011-0165585 A1), which is a U.S. national phase of International Application No. PCT/EP2009/057225, filed Jun. 11, 2009, which designated the U.S. and claims priority to EP 08158028.4, filed Jun. 11, 2008, the entire contents of each of which are hereby incorporated by reference.

FIELD OF THE INVENTION

The present invention relates to new nucleic acid sequences which are able to drive gene expression in several industrially relevant species.

BACKGROUND OF THE INVENTION

To optimize the production of various compounds of interest recombinant DNA technologies provide for a very relevant toolbox. These tools allow for the efficient modification of genomic DNA in such way that various alterations are possible. Among these are: overexpression of a homologous gene, overexpression of a heterologous gene, deletion of a homologous gene, block a metabolic route to a unwanted side product, diversion of a metabolic route. Although fairly efficient there is a common drawback in all these methods: they use host species-specific regulation systems. If one wants to test the properties of an enzyme encoded by a certain gene this is most often done in one species; the favorite species of the laboratory. If such a gene is obtained from a different donor species, quite often codon optimalisation is needed to allow expression of this enzyme in the new host (see for example: Sinclair & Choy. 2002. Protein Expr Purif. 26:96-105). With the decreasing costs of synthetic DNA this becomes a feasible approach for known genes, still the average costs are around 1000 US dollars per gene (assuming an average gene length of 1.5-2.0 kb). There are however cases where this will not help: (i) if the gene sequence/s is/are unknown, i.e. in metagenomic screening projects; (ii) if the protein needs donor-specific chaperones or helper enzymes, like P450 enzymes; (iii) if the DNA, RNA-intermediates and/or enzyme is toxic to the new host; (iv) if the folding of the enzyme is crucial for the activity and not possible by the new host; (v) if one wants to compare many known enzymes the total costs of synthetic DNA will become very high again, i.e. 1000 synthetic genes cost 1 million US dollar.

One solution to increase the chance of success, without the costs of synthetic DNA, is to test the enzyme(s) expression in several different species; this increases the chance of successful expression of each enzyme at least in one of the hosts. However, chance of successful expression of each enzyme at least in one of the hosts. However, current state-of-the-art tools allow only for species-specific expression cassettes. For each host a species-specific promoter is used and this leads to too much cloning work if one wants to evaluate the same enzyme(s) in multiple organisms.

New technologies might make this latter problem less of a burden; by using the efficient modern recombination systems (for example the Gateway System of Invitrogen) it should be relatively easy to transfer gene(s) of interest from one plasmid to a range of plasmids all having a species-specific promoter system. However, in practice this involves still quite some laboratory procedures, especially when one want to test hundreds to thousands genes of interest. And with the rapid availability of many genome sequences and the constant need of industrial biocatalysis for new enzymes with optimal kinetics it is crucial that one can do so. Moreover, technologies like Gateway insert a stretch of nucleotides (20-30 bp) between promoter and gene-of-interest, which can severely hamper the transcription and/or translation of the gene.

So, there is a need for a new, low-cost and High Throughput technology allowing the evaluation and/or application of enzymes in multiple different hosts.

A solution might be a promoter that can function in a wide range of species. By using such system one could make one expression cassette (or one metagenomic library) and transform this to a range of species and test the activity of the enzyme. Examples of ease of use would be (a) efficient enzyme screening, viz. cloning genes of interest behind a promoter; first test in *E. coli* and then transfer to various industrial hosts to isolate the best expression host and directly see how the enzyme will function in the later industrial cell-environment; (b) functional genomics. With the availability of full genome sequences there is a growing need for High Throughput gene function studies. These uses all rely on two crucial steps: efficient cloning steps in a workhorse (like *E. coli*, to produce knockout cassettes) and introduction into the host. However, both species use different selection marker cassettes due to cross-species barriers; a commonly used selection marker cassette would be very convenient Both Examples given can only succeed if promoter systems would function in a very wide range of hosts. However, there seem to be some crucial differences in promoter organization between species; for example between eukaryotes and prokaryotes. The latter group most often relies on the so-called −10/−35 sequences and a transcription start site, while the former group, although with a lot of variation, has a minimum requirement of a functional TATA-box. But also within these two groups there are various differences. In the group of eukaryotes other sequences might be present or not, like so-called CAAT-boxes, GC-boxes and Kozak-sequences. This causes quite some differences between for example a fungal and a mammalian promoter sequence. Also in the group of prokaryotes there are many differences. For example *E. coli* is a very 'promiscuous' species; it has a very relaxed acceptance of different promoter structures and varying distances between promoter and gene, making it such a well-loved screening work horse. But species like *Bacillus* are much more stringent, while the wide metabolic diversity of *Streptomyces* might have evolved into an extremely wide range of promoter structures making it impossible to extract common (and predictive) features in this group. On top of this, every species has its own specific, and sometimes peculiar, regulatory systems. These basic elements are generally determining if the gene downstream of the promoter is actually transcribed or repressed, depending on the actual information the cell obtains from the environment. So, in practice there might be sequences in a promoter which are not recognized by any of the cell's machinery in one host, while in another host this would be the basis of a very strong and unwanted transcriptional regulation.

There are examples in literature of promoter systems that do work in two or three different species but this is limited to few and related species. For example, Asturias et al., 1990, FEMS Microbiol Lett 56: 65-68, Alvarez et al, 1994, FEMS Microbiol Lett. 115: 119-124 and Patek et al., 2003, J Biotechnol 104: 325-334 describe promoters which are active in prokaryotes only. Hamer et al., 2001, Proc Natl Acad Sci USA 98: 5110-5115 discloses a promoter which is active in one eukaryote and one prokaryote, like *Magneportha grisea* and *E. coli*. Thus, in most cases the examples are either limited to prokaryotes only, to two species (i.e. a laboratory 'work-horse' and a final host) or to very specific isolated promoter regions, or need specific cultivation conditions. Some engineered promoters are made via fusion: simply clone the eukaryotic and the prokaryotic promoter back-to-back, which therefore maintain their peculiar donor-specific regulation systems which might have a negative impact in other hosts.

But also examples of non-compatibility, even between prokaryotes, have been reported. Examples can be found for: *E. coli* and *Brevicompactum* (Azza et al., 1994, FEMS Microbial Lett 122: 129-136), *S. lividans* and *E. coli* (Asturias et al., 1990). This shows that even within the related class of prokaryotes there are differences, for example between gram-positives and gram-negatives.

So, although Examples of multi-species promoters are known there is no promoter available which does function in a wide range of species of industrial relevance (i.e. active in multiple prokaryotes and multiple eukaryotes), although this is highly desirable. Moreover, in the specific application of combining such a promoter to selection markers the Examples in literature are only for dominant (i.e. antibiotic) selection markers, while there is a growing need for (a) non-antibiotic markers and (b) markers which enable both forward and backward selection (i.e. selection for the presence or the absence of the marker gene), allowing an efficient marker-removal after the gene-of-interest is stably integrated in the hosts genome.

DETAILED DESCRIPTION OF THE INVENTION

Several terms used in the present description and claims are defined as follows.

The term "gene-of-interest" or "gene" is herein defined as a polynucleotide sequence encoding a polypeptide, irrespective of whether the DNA sequence is a cDNA, a genomic DNA or a synthetic DNA sequence, which may contain one or more introns.

The term "polynucleotide sequences with promoter activity" is herein defined as a polynucleotide sequence driving transcription of a down-stream gene-of-interest.

The term "selection marker gene" (or selectable marker gene) is herein defined as a gene-of-interest that encodes a polypeptide that provides a phenotype to the cell containing the gene such that the phenotype allows either positive or negative, selection of cells containing the selection marker gene. The selection marker gene may be used to distinguish between transformed and non-transformed cells or may be used to identify cells having undergone recombination or other kinds of genetic modifications.

An "acetamidase" is herein defined as an enzyme which is capable of catalysing the hydrolysis of acetamide into acetic acid and ammonium, and/or which is capable of catalysing the hydrolysis of related amide-compounds such as acrylamide.

An "amdS gene" is herein defined as a gene-of-interest, which is preferably obtainable from a microbial origin or via synthetic DNA, and which encodes a polypeptide that is an acetamidase as defined above. Preferably, an amdS gene shows sequence similarity with one or more of the filamentous fungal amdS genes known in the art, i.e. the amdS genes from *A. nidulans, A. oryzae, A. niger, P. chrysogenum* or the amdS-like gene from *S. cerevisiae*. An amdS gene preferably encodes a protein of about 500 to 600 amino acids. An amdS gene is therefore usually contained within a DNA fragment of about 2.0 kb. The presence of introns in a genomic amdS gene can increase the length to e.g. about 2.5 kb or more. An "amdS gene" is an Example of a "selection marker gene".

A "ble gene" is herein defined as a gene-of-interest, which is preferably obtainable from a microbial origin or via synthetic DNA, and which encodes a polypeptide that is a bleomycin or phleomycin binding protein, which provides resistance to these toxic molecules. Preferably, a ble gene shows sequence similarity with one or more of the known ble genes known in the art, i.e. the ble genes from transposon Tn5, *Streptomyces verticillus, Staphylococcus aureus* or *Streptoalloteichus hindustanus*. A ble gene preferably encodes a protein of about 100 to 150 amino acids. A ble gene is therefore usually contained within a DNA fragment of about 0.4 kb. A "ble gene" is an Example of a "selection marker gene".

The term "Gateway recombination" or "Gateway reaction" herein is used to refer to the Gateway® recombination cloning technology of Invitrogen.

The term "STABY cloning" or "STABY reaction" herein is used to refer to the STABY™ cloning technology of Eurogentec.

Polynucleotide Sequences of the Invention

The present invention provides in a first aspect for polynucleotide sequences of the general formula $$T\text{-}T\text{-}G\text{-}A\text{-}C\text{-}W\text{-}N(o)\text{-}Y_1\text{-}A\text{-}Y_2\text{-}A\text{-}A\text{-}T\text{-}H_1\text{-}H_2\text{-}N(p)\text{-}S_1\text{-}S_2\text{-}W\text{-}K_1\text{-}K_2\text{-}N(q)\text{-}H_3\text{-}M_1\text{-}M_2\text{-}H_4\text{-}A\text{-}T\text{-}G,$$ 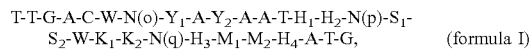(formula I)

wherein

N is any of the nucleotides A, C, G and T, and N(o) is 16, 17 or 18 nucleotides long; N(p) is 21, 22 or 23 nucleotides long; N(q) is 2, 3, 4, 5 or 6 nucleotides long; and each individual N in N(o), N(p), and N(q) are the same or different;

W is any of the nucleotides A and T;

Y is any of the nucleotides C and T, and $Y_1$ and $Y_2$ are the same or different;

H is any of the nucleotides A, C, and T and $H_1$, $H_2$, $H_3$ and $H_4$ are the same or different;

S is any of the nucleotides G and C, and $S_1$ and $S_2$ are the same or different;

K is any of the nucleotides G and T, and $K_1$ and $K_2$ are the same or different;

M is any of the nucleotides A and C, and $M_1$ and $M_2$ are the same or different;

The AG-content of N(o) is below 50%

The A-content of N(o) is below 35%

The AG-content within each stretch of 6 nucleotides in N(o) is below 66%

The AG-content of N(p) is below 60%

The AG-content within each stretch of 6 nucleotides in N(p) is below 83%

N(o) and N(p) do not contain two consecutive G's

The G-content of N(q) is below 50%.

These polynucleotide sequences of the invention have the great advantage that when present in a polynucleotide control sequence, such as a promoter, the control sequence will direct expression in a wide range of industrially relevant species, in both prokaryotes and eukaryotes. Moreover when applied in combination with selection marker genes one can perform selectable cloning in a laboratory host (for example making deletion constructs in *E. coli*) and use the same construct in the final host. Also, for genes encoding enzymes like acetamidase (for example the *Aspergillus nidulans* amdS gene), which enzyme enables both forward and backward selection (i.e. selection for the presence or the absence of the enzyme), the polynucleotide control sequences of the present invention provide for a very efficient selection marker cassette which can be used in a wide range of industrially relevant species.

In one embodiment, the polynucleotide sequences of the invention have formula I, wherein
N is any of the nucleotides A, C, G and T, and N(o) can be 16, 17 or 18 nucleotides long;
N(p) can be 21, 22 or 23 nucleotides long; N(q) can be 2, 3, 4, 5 or 6 nucleotides long;
and each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 40%;
The A-content of N(o) is below 25%;
The AG-content within each stretch of 6 nucleotides in N(o) is below 50%;
The AG-content of N(p) is below 50%;
The AG-content within each stretch of 6 nucleotides in N(p) is below 70%;
N(o) and N(p) do not contain two consecutive G's;
The G-content of N(q) is below 50%.

In another embodiment, the polynucleotide sequences of the invention have formula I, wherein
N is any of the nucleotides A, C, G and T, and N(o) can be 16, 17 or 18 nucleotides long;
N(p) can be 21, 22 or 23 nucleotides long; N(q) can be 2, 3, 4, 5 or 6 nucleotides long;
and each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 25%;
The AG-content within each stretch of 6 nucleotides in N(o) is below 50%;
The AG-content of N(p) is below 25%;
The AG-content within each stretch of 6 nucleotides in N(p) is below 50%;
N(o) and N(p) do not contain two consecutive G's;
The G-content of N(q) is below 50%.

In yet another embodiment, the polynucleotide sequences of the invention have formula I, wherein
N is any of the nucleotides A, C, G and T, and N(o) can be 16, 17 or 18 nucleotides long;
N(p) can be 21, 22 or 23 nucleotides long; N(q) can be 2, 3 or 4 nucleotides long; and
each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 50%;
The A-content of N(o) is below 35%;
The AG-content within each stretch of 6 nucleotides in N(o) is below 66%;
The AG-content of N(p) is below 60%;
The AG-content within each stretch of 6 nucleotides in N(p) is below 83%;
N(o) and N(p) do not contain two consecutive G's;
The G-content of N(q) is below 50%.

In yet another embodiment, the polynucleotide sequences of the invention have formula I, wherein
N is any of the nucleotides A, C, G and T, and N(o) is 16, 17 or 18 nucleotides long; N(p) is 21, 22 or 23 nucleotides long; N(q) is 2, 3 or 4 nucleotides long; and each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 25%;
The AG-content within each stretch of 6 nucleotides in N(o) is below 50%;
The AG-content of N(p) is below 25%;
The AG-content within each stretch of 6 nucleotides in N(p) is below 50%;
N(o) and N(p) do not contain two consecutive G's;
The G-content of N(q) is below 50%.

Preferably, the polynucleotide sequences of the invention have formula I, wherein
N is any of the nucleotides A, C, G and T, and N(o) is 17 nucleotides long; N(p) is 23 nucleotides long; N(q) can be 3 or 4 nucleotides long; and each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 50%;
The A-content of N(o) is below 35%;

The AG-content within each stretch of 6 nucleotides in N(o) is below 66%;
The AG-content of N(p) is below 60%;
The AG-content within each stretch of 6 nucleotides in N(p) is below 83%;
N(o) and N(p) do not contain two consecutive G's;
The G-content of N(q) is below 50%.

More preferably, the polynucleotide sequences of the invention have formula I, wherein
N is any of the nucleotides A, C, G and T, and N(o) is 17 nucleotides long; N(p) is 23 nucleotides long; N(q) is 3 or 4 nucleotides long; and each individual N in N(o), N(p), and N(q) are the same or different;
W is any of the nucleotides A and T;
Y is any of the nucleotides C and T, and $Y_1$ and $Y_2$ are the same or different;
H is any of the nucleotides A, C, and T and $H_1$, $H_2$, $H_3$ and $H_4$ are the same or different;
S is any of the nucleotides G and C, and $S_1$ and $S_2$ are the same or different;
K is any of the nucleotides G and T, and $K_1$ and $K_2$ are the same or different;
M is any of the nucleotides A and C, and $M_1$ and $M_2$ are the same or different;
The AG-content of N(o) is below 50%;
The A-content of N(o) is below 35%;
The AG-content within each stretch of 6 nucleotides in N(o) is below 66%;
The AG-content of N(p) is below 60%;
The AG-content within each stretch of 6 nucleotides in N(p) is below 83%;
N(o) and N(p) do not contain two consecutive G's;
The G-content of N(q) is below 50%;
No stretch of 6 nucleotides is exactly matching SYGGRG, wherein R can be any of the nucleotides A and G.

In a preferred embodiment, the polynucleotide sequences of the invention are selected from the group consisting of SEQ ID No. 1 to 51, 76 and 77. More preferably the polynucleotide sequences are selected from the group consisting of SEQ ID No. 46-51, 76 and 77. Most preferably, the polynucleotide sequence of the invention has a sequence as shown in SEQ ID No. 48. Also polynucleotides which have a sequence which is substantially homologous to a polynucleotide sequence of the invention are encompassed by the present invention. A polynucleotide having a polynucleotide sequence that is "substantially homologous" to a polynucleotide sequence of the invention is defined as a polynucleotide having a polynucleotide sequence possessing a degree of identity to a polynucleotide sequence of the invention of at least 30%, preferably of at least 35%, more preferably of at least 40%, at least 45%, at least 50%, or at least 55%. Still more preferably of at least 60%, at least 65%, at least 70%, at least 75%, at least 80%, at least 85% or at least 90%. Even still more preferably of at least 95%, at least 96%, or at least 97%. Most preferably of at least 98% or at least 99%, whereby the substantially homologous polynucleotide sequence displays promoter activity.

A substantially homologous polynucleotide sequence may encompass polymorphisms that may exist in cells from different populations or within a population due to natural allelic or intra-strain variation. A substantially homologous polynucleotide sequence may further be derived from a natural source or may be artificially designed and synthesized.

For the purpose of the present invention, the degree of identity between two polynucleotide sequences refers to the percentage of nucleotides that are identical between the two sequences. The degree of identity is determined using the BLAST algorithm, which is described in Altschul et al. 1990. J. Mol. Biol. 215: 403-410. Software for performing BLAST analyses is publicly available through the National Center for Biotechnology Information (http://www.ncbi.nlm.nih.gov/). The BLAST algorithm parameters W, T, and X determine the sensitivity and speed of the alignment. The BLAST program uses as defaults a word length (W) of 11, the BLOSUM62 scoring matrix (see Henikoff & Henikoff. 1989. Proc. Natl. Acad. Sci. USA 89: 10915) alignments (B) of 50, expectation (E) of 10, M=5, N=−4, and a comparison of both strands. Preferably, the comparison is done using specific software for comparing short DNA fragments; for example using the program Fuzznuc, available through The European Molecular Biology Open Software Suite website (via http://emboss.bioinformatics.nl/).

Polynucleotide sequences related to the polynucleotide sequences of the invention and obtained by insertion, addition and/or deletion of small stretches of nucleotides are also part of the invention. Such insertions, additions and/or deletions may vary in length, for example from 1-1000 nucleotides, preferably 1-100 nucleotides, more preferably from 1-20 nucleotides, even more preferably from 1-10 nucleotides, still more preferably from 1-6 nucleotides and most preferably from 1-3 nucleotides, still leading to a biologically active polynucleotide sequences with promoter activity. Also, functional parts of the specified polynucleotide sequences are part of the invention. Such functional parts can be shortened from either end of the polynucleotide sequence of the invention by, for example, 1-50 nucleotides, preferably 1-30 nucleotides, more preferably 1-25 nucleotides, even more preferably 1-20 nucleotides, still more preferably 1-15 nucleotides, still more preferably 1-10 nucleotides and most preferably 1-5 nucleotides.

In one embodiment, the polynucleotide sequences of the invention are part of longer polynucleotide constructs, such as polynucleotide control sequences wherein for example 5' extensions are added or for example 3' extensions are added. These are discussed below.

A specific embodiment of the current invention describes polynucleotide control sequences with "improved functionality". "Improved functionality" covers a range of typical promoter aspects. These include, but are not limited to: sequences recognized by trans- or cis-activating transcription factors; stabilizing elements; chromatin remodeling elements; AT-rich elements. Such elements can be introduced on purpose (via targeted cloning, fusion with other promoters or synthetic DNA design) or at random (via mutagenesis, error prone PCR and/or directed evolution), followed by proper screening assays to isolate the polynucleotide control sequences with "improved functionality". Particular useful are full synthetic libraries of variants of active promoters.

The polynucleotide or nucleic acid sequence of the invention may be an isolated polynucleotide of genomic, cDNA, RNA, semi-synthetic, synthetic origin, or any combinations thereof. The term "isolated polynucleotide or nucleic acid sequence" as used herein refers to a polynucleotide or nucleic acid sequence which is essentially free of other nucleic acid sequences, e. g., at least about 20% pure, preferably at least about 40% pure, more preferably at least about 60% pure, even more preferably at least about 80% pure, most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced.

Polynucleotide Control Sequences and Nucleic Acid Constructs According to the Invention In another aspect, the invention provides for polynucleotide control sequences which comprise a polynucleotide sequence or a polynucleotide construct of the invention. The term "control sequences" is defined herein to include all components which are necessary or advantageous for the expression of a polypeptide. "Expression" will be understood to include any step involved in the production of the polypeptide and may include transcription, post-transcriptional modification, translation, post-translational modification, fusion, multimerization, maturation, and secretion. A polynucleotide control sequence according to the invention may be native or foreign to the nucleic acid sequence encoding the polypeptide. Suitable Examples of control sequences include, but are not limited to, a promoter sequence, a leader, optimal translation initiation sequences (as described in Kozak. 1991. J. Biol. Chem. 266:19867-19870), a secretion signal sequence, a pro-peptide sequence, a polyadenylation sequence, a transcription terminator.

In a preferred embodiment, the control sequence of the invention is part of a nucleic acid construct. Nucleic acid constructs according to the invention contain a gene-of-interest operably linked to the polynucleotide control sequence of the invention which directs the expression of the gene-of-interest encoded polypeptide in a suitable (expression) host.

The term "nucleic acid construct" is synonymous with the term "expression vector" or "expression cassette" when the nucleic acid construct contains all the control sequences required for expression of a coding sequence in a particular host organism. The expression vector may be any vector (e.g. a plasmid or virus) which can be conveniently subjected to recombinant DNA procedures and can bring about the expression of the nucleic acid sequence encoding the polypeptide. The choice of the vector will typically depend on the compatibility of the vector with the cell into which the vector is to be introduced. The vectors may be linear or closed circular plasmids.

The vector may be an autonomously replicating vector, i.e. a vector, which exists as an extrachromosomal entity, the replication of which is independent of chromosomal replication, e.g. a plasmid, an extrachromosomal element, a minichromosome, or an artificial chromosome.

Alternatively, the vector may be one which, when introduced into the cell, is integrated into the genome and replicated together with the chromosome (s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least at least 0.1 kb, even preferably at least 0.2 kb, more preferably at least 0.5 kb, even more preferably at least 1 kb, most preferably at least 2 kb.

The term "operably linked" is defined herein as a configuration in which a control sequence is appropriately placed at a position relative to the coding sequence of the sequence gene-of-interest such that the control sequence directs the production of a polypeptide. It should be clear to those skilled in the art that transcriptional and translational stop signals are not always well defined and also not need to be specifically added to the gene-of-interest sequence, although specific addition can increase the overall efficiency polypeptide production. The polynucleotide control sequence preferably contains part of or the complete polynucleotide sequence of the invention. The polynucleotide control sequence may be any nucleic acid sequence, which shows transcription regulatory activity in the cell including mutant, truncated, and hybrid promoters, and may be obtained from any source, including but not limited to genomic DNA, synthetic DNA, copy DNA. The polynucleotide control sequence may be either homologous or heterologous to the cell or to the gene-of-interest.

The control sequence may also include a suitable transcription terminator sequence, a sequence recognized by the various host cells to terminate transcription. The terminator sequence is operably linked to the 3' terminus of the gene-of-interest encoding the polypeptide. Any terminator, which is functional in the various host cells, may be used in the present invention.

The control sequence may also include a suitable signal sequence, a translated region, which is important for intracellular trafficking. The signal sequence is operably linked to the 5' terminus of the gene-of-interest encoding the polypeptide. Any signal sequence, which is functional in the various host cells, may be used in the present invention.

The control sequence may also include a suitable cleavage sequence, a translated region, which is important for post-translational modification. The signal sequence is operably linked to the 5' or the 3' terminus of the gene-of-interest encoding the polypeptide, depending on the mode of activity. Any signal sequence, which is functional either in the various host cells or in vitro, may be used in the present invention.

The control sequence may also include a suitable tag sequence, a translated region, which is important for purification in vitro. The tag sequence is operably linked to the 5' or 3' terminus of the gene-of-interest encoding the polypeptide. Alternatively, the tag sequence can be inserted within the polypeptide sequence. Any tag sequence, which is functional in the various host cells, may be used in the present invention.

The control sequence may also include a polyadenylation sequence, a sequence which is operably linked to the 3' terminus of the gene-of-interest and which, when transcribed, is recognized by host cells as a signal to add polyadenosine residues to transcribed mRNA. Any polyadenylation sequence, which is functional in the cell, may be used in the present invention.

The polynucleotide control sequences of the invention drive expression in at least three different species. Preferably, they drive expression in at least four different species. More preferably, polynucleotide control sequences of the invention drive expression in at least five different species. Even more preferably, polynucleotide control sequences of the invention drive expression in at least six different species. Still more preferably, polynucleotide control sequences of the invention drive expression in at least eight different species. Most preferably, polynucleotide control sequences of the invention drive expression in at least ten different species.

Preferred polynucleotide control sequences are polynucleotide control sequences which drive expression of polypeptides in at least three of the following groups: mammals, planta, algae, fungi, yeasts, gram-positive bacteria, gram-negative bacteria or archaebacteria. More preferably, polynucleotide sequences that drive expression in four or more of these groups. Even more preferably, polynucleotide sequences that drive expression in five or more of these groups. Still more preferably, polynucleotide sequences that drive expression in six or more of these groups. Most preferably, polynucleotide sequences that drive expression in all seven groups.

In another preferred embodiment, polynucleotide control sequence according to the invention direct the expression of polypeptides in at least four of the following genera: *Escherichia, Streptomyces, Bacillus, Gluconobacter, Pseudomonas, Clostridium, Saccharomyces, Kluyveromyces, Pichia, Penicillium, Aspergillus, Mortierella, Chrysosporium, Acremonium, Trichoderma, Cricetulus, Homo.*

Particular Genes-of-Interest in the Nucleic Acid Constructs According to the Invention The gene-of-interest in the nucleic acid constructs according to the invention may be any gene which encodes a relevant polypeptide.

In one embodiment, the gene-of-interest is a selection marker gene. Preferably one or more of the following selection marker genes are used: ble, nptII, bla, amdS, URA3, TRP1, LEU2 and pyrG, including all the substantially homologous and functional analogous variants of the known genes, including synthetic and codon-adapted variants). More preferably, the gene-of-interest is a ble gene or acetamidase gene. The ble gene is a very convenient selection marker gene because it is small and the advantage of the acetamidase gene is that both forward and backward selection is possible. This means that apart from the positive selection for the presence of the amdS gene using acetamide as the sole carbon or nitrogen source, a counter selection can be applied using fluoracetamide to select against the presence of the amdS gene; (see for example WO 97/06261).

In one embodiment, the gene-of-interest is the *Aspergillus nidulans* amdS gene, but any other gene encoding a polypeptide having a similar enzymatic activity will be suitable. This is not only limited to an amino acid sequence that is "substantially homologous" to the sequence of *A. nidulans* amdS, but also the "functional analogues".

In this context, "functional analogues" are defined as polypeptides having an amino acid sequence possessing the capability of hydrolyzing acetamide or fluoracetamide. Also polypeptides able to hydrolyze analogous substances as acrylamide, adipamide or formamide should be considered under this definition. "Substantially homologous" is defined as polypeptides having an amino acid sequence possessing a degree of identity to the specified amino acid sequence of at least 30%, preferably at least 40%, more preferably at least 50%, still more preferably at least 60%, still preferably at least 70%, still more preferably at least 80%, still more preferably at least 90%, still more preferably at least 95% and most preferably at least 99%, the substantially homologous peptide displaying acetamidase activity and providing a reverse selection on fluoroacetamide. A substantially homologous polypeptide may encompass polymorphisms that may exist in cells from different populations or within a population due to natural allelic or intra-strain variation. A substantially homologous polypeptide may further be derived from a fungus other than the fungus where the specified amino acid and/or DNA sequence originates from, or may be encoded by an artificially designed and synthesized DNA sequence. DNA sequences related to the specified DNA sequences and obtained by degeneration of the genetic code are also part of the invention. Homologues may also encompass biologically active fragments of the full-length sequence. Of course, the scope of the invention is not limited to the specific selection marker genes used in the Examples. The person skilled in the art will understand that in principle any selection marker gene may be used, including but not limited to dominant, recessive, antibiotic, metabolic, and fluorescent marker genes.

In another embodiment, the gene-of-interest is a gene encoding a metabolic enzyme, a transcription factor, a cell cycle protein, a protease, a cellulase or an antibody.

In yet another embodiment, the gene-of-interest is a gene encoding a pharmaceutical protein or an enzyme involved in the production of a pharmaceutical.

The polynucleotide sequence or control sequence of the invention may be fused to the gene-of-interest. This is particularly convenient in transfection experiments.

In one embodiment, a polynucleotide control sequence of the invention is fused to a selection marker gene. The selection marker gene may be any selection marker gene, but is preferably an amdS gene or a ble gene.

Methods for Obtaining a Polynucleotide or Polynucleotide Control Sequence According to the Invention In yet another aspect, the present invention provides for a method of obtaining polynucleotide sequences of the invention. A polynucleotide sequence according to the invention may be obtained from any species.

Polynucleotide sequences of the invention may be obtained by hybridization. Nucleic acid molecules corresponding to variants (e.g. natural allelic variants) and homologues of the polynucleotides of the invention can be isolated based on their homology to the nucleic acids disclosed herein using these nucleic acids or a suitable fragment thereof, as a hybridization probe according to standard hybridization techniques, preferably under highly stringent hybridization conditions. Alternatively, one could apply in silico screening through the available genome databases.

"Stringency" of hybridization reactions is readily determinable by one of ordinary skill in the art. For additional details and explanation of stringency of hybridization reactions, see Ausubel et al. 1995. Current Protocols in Molecular Biology, Wiley Interscience Publishers.

The nucleic acid sequence may be isolated by e.g. screening a genomic library of the microorganism in question. Once a nucleic acid sequence encoding a polypeptide having an activity according to the invention has been detected with e.g. a probe derived from SEQ ID NO 1 or 51, the sequence may be isolated or cloned by utilizing techniques which are known to those of ordinary skill in the art (see Sambrook et al. 1989, Molecular Cloning, A Laboratory Manual, 2d edition, Cold Spring Harbor, N.Y.).

The cloning of the nucleic acid sequences of the present invention from such (genomic) DNA can also be effected, e.g. by using methods based on polymerase chain reaction (PCR) or antibody screening of expression libraries to detect cloned DNA fragments with shared structural features (see Innis et al. 1990. PCR: A Guide to Methods and Application, Academic Press, New York.).

The sequence information as provided herein should not be so narrowly construed as to require inclusion of erroneously identified bases. The specific sequences disclosed herein can be readily used to isolate the complete polynucleotide or nucleic acid sequence, which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. The person skilled in the art is capable of identifying such erroneously identified bases and knows how to correct for such errors.

In one embodiment suitable polynucleotide sequences of the invention are designed in silico in such a way that they have a certain length and are combined with suitable control sequences. Such polynucleotide sequences can be made synthetically and cloned in front of any gene of interest.

In a preferred embodiment, the polynucleotide sequence may be derived from a natural gene which is expressed at high levels (characterized by an mRNA concentration of at least 0.5% (w/w) of the total cellular mRNA) in a certain species. In another preferred embodiment, the promoter may be derived from a natural gene which is expressed at medium level (characterized by an mRNA concentration in the range of 0.01% to 0.5% (w/w) of the total cellular mRNA). In another preferred embodiment, the promoter may be derived from a natural gene, which is expressed at low levels (characterized by an mRNA concentration lower than 0.01% (w/w) of the total cellular mRNA).

In an even more preferred embodiment, Micro Array data is used to select genes, and thus polynucleotide control sequences of those genes, that have a certain transcriptional level and regulation. In this way one can adapt the gene expression cassettes optimally to the conditions it should function in.

Alternatively, random DNA fragments may be cloned in front of the selectable marker genes, for example an antibiotic resistance marker gene like the ble gene, encoding for a protein that provides resistance towards compounds like zeocin, bleomycin and phleomycin. This is a selection marker gene which is used in several species (fungi, yeasts, bacteria), although with species specific promoters. Using selective growth conditions one can easily select for active polynucleotide control sequences, as these should facilitate growth on media containing zeocin (or phleomycin or bleomycin or any suitable alternative compound) in such a concentration that it will inhibit growth of the parent cell or cells with a non-functional promoter. These DNA fragments can be derived from many sources, i.e. different species, PCR amplified, synthetically and the like.

The polynucleotide sequences of the invention obtained by the various methods may be used as polynucleotide control sequences and tested in several species. This can be done in parallel, but with high numbers and a good selection system this is preferably done in a serial mode. After selecting active polynucleotide control sequences of the invention in a first species, the DNA can be isolated and used to transfect a second species. Using the right selective pressure only a subset of the first selected promoters will be obtained, but these will drive transcription in both the first and second species. This procedure can be continued until one has isolated a polynucleotide control sequences of the invention that drives expression in all of the selected hosts.

Host Cells According to the Invention

In a further aspect, the present invention relates to a host cell which comprises a polynucleotide sequence, a polynucleotide construct, a polynucleotide control sequence, an expression cassette or a vector according to the present invention and which is suitable for producing a compound of interest. The host may be any host, be it a prokaryote or an eukaryote organism. Preferably the host is an *E. coli*, a *B. subtilis*, a *S. cerevisiae* or a *P. chrysogenum*. In a preferred embodiment, the host is optimized for targeted integration; Examples of suitable host are well-known in the art, for example from WO05/095624, which is incorporated herein by reference.

The host cell may be used for producing suitable compounds of interest, including for example a polypeptide, an antibody or a primary or secondary metabolite, such as a pharmaceutical compound.

Uses of the Polynucleotide Sequences of the Invention

In yet another aspect of the present invention, a polynucleotide sequence, a polynucleotide construct, a polynucleotide control sequence, an expression cassette or a vector according the invention, collectively called the polynucleotide molecules of the invention, or a host cell of the invention are used in cloning reactions, in restriction enzyme digestion, in recombination reactions, in molecular biology kits and reagents, in enzyme screening, in biocatalysis reactions, in biochemical reactions, or in a fermentation process.

The polynucleotide molecules and the host cell of the invention may advantageously be used in a method for in vitro or in vivo cloning experiments. The combination of expression cassettes consisting of polynucleotide control sequences fused to the selection marker genes has many advantages. It significantly enhances the success rate of classical restriction enzyme and ligation cloning, it enhances the success rate single and multiple fragment Gateway recombination reactions, enables efficient multiple fragment STABY cloning reactions.

The scope of the present invention is not limited to the specific cloning methods disclosed in Examples, but also include other cloning (commercial) methods such as TOPO cloning, RED/ET recombination, In Fusion cloning and Yeast Recombination cloning.

Fusion constructs between polynucleotide control sequences of the invention and selection marker genes are particular useful to construct gene-of-interest overexpression or deletion constructs. For example, gene deletions via the so-called double cross over method (Rothstein. 1983. Meth. Enzymol. 101:202-211) can be easily created in a suitable laboratory workhouse like *E. coli* using the same selection marker gene expression cassette as will be used in the actual deletion of the target gene in the final host (see for details Example 13). The advantage is that one can already select for the correct construct in *E. coli* enabling a faster throughput and a higher success rate. If the selection marker gene expression cassette is surrounded by direct repeats or recombination sites, such as LOX sites or similar (see http://en.wikipedia.org/wiki/Cre-Lox_recombination) it is possible to quickly remove the selection marker gene expression cassette once the correct integration has been obtained. A highly preferred selection marker gene for that purpose is a bidirectional selection marker gene encoding a polypeptide enabling both forward and backward selection, such as for examples the acetamidase genes. The preferred method for such forward and backward selection is described in WO97/06261 which is incorporated herein by reference. Preferred acetamidase genes are acetamidase genes with improved selection characteristics. These are known in the art, for example from WO2007/118836, which is incorporated herein by reference. Preferably, improved selective media are used, because this significantly decreasing any background, if present.

In a yet another aspect of the present invention the polynucleotide sequence, the polynucleotide control sequence or the nucleic acid cassette of the present invention is used in a method for to screen for new enzyme activities.

Specific gene(s)-of-interest may be cloned under control of the polynucleotide sequence, the polynucleotide control sequence or the nucleic acid cassette of the present invention in a method for driving expression of the polypeptides in various hosts. As some polypeptides are not properly expressed in some hosts it is an advantage not having to optimize the expression cassettes for every host, but just produce one expression cassette which one can test in various host. The number and source of gene(s)-of-interest is per definition unlimited. It could be a selection of known genes one can PCR amplify or obtain via synthetic DNA (say 1-1000 genes); it could be a metagenomic library (consisting of 10,000-10,000,000 unknown polynucleotide sequences); it could be a library of variants from a single gene (for example 200-20.000 variants obtained via error-prone PCR, directed evolution or gene shuffling); it could be a library of untranscribed genes (while many of the genes of the sequenced genomes are not transcribed under the conditions studied, they still might have highly interesting enzyme activities, so placing them behind a functional promoter will enable them to be screened);

For example, one can clone 1000 protease genes from various sources under control of a polynucleotide sequence of the first or second aspect. To increase the percentage of genes successfully expressed so a proper screening process is allowed one can transform this library to a selection of suitable hosts for proteases, i.e. B. subtilis, E. coli, S. cerevisiae and A. niger, and the promoter will drive transcription of all 1000 genes in all these species.

In one specific embodiment the screen is for intracellular polypeptides.

In another specific embodiment the screen is for secreted polypeptides. For a polypeptide to be secreted, the control sequence may also include a signal peptide-encoding region, which codes for an amino acid sequence linked to the amino terminus of the polypeptide, which can direct the encoded polypeptide into the cell's secretory pathway. The 5' end of the coding sequence of the gene may inherently contain a signal peptide-coding region naturally linked in translation reading frame with the segment of the coding region, which encodes the secreted polypeptide. Alternatively, the 5' end of the gene may contain a signal peptide-coding region, which is foreign to the coding sequence. The foreign signal peptide-coding region may be required where the gene does not normally contain a signal peptide-coding region. Alternatively, the foreign signal peptide-coding region may simply replace the natural signal peptide-gene in order to obtain enhanced secretion of the polypeptide.

SHORT DESCRIPTION OF THE FIGURES

FIG. 1 shows the effect of removing the glucose repression from the *Penicillium chrysogenum* pcbC promoter. (A). the relevant 756 bases of the pcbC promoter. The putative creA sites are underlined and below are the basepair changes indicated in capitals (changed into EcoRI and MunI site, respectively). The relevant introduced restriction sites for cloning (NdeI and ClaI) are also indicated below the original sequence. The ATG is indicated in capitals and bold. Also, indicated is the introduced HpaI site in front of the ATG. (B). rtPCR on samples from strain with wild type promoter construct; (C). rtPCR on samples from strain with creA mutant promoter construct Legend: G=glucose; L=Lactose FIG. 2 shows the relevant parts of the fungal promoters and the bacterial promoter inserts. (A). the 3' part of the *A. nidulans* gpdA promoter with the CAT nucleotides inserted in front of the ATG to obtain a NdeI site. (B). the essential part of the *B. subtilis* PE4 promoter with the bacterial consensus elements underlined. (C). the 3' part of the *P. chrysogenum* pcbCΔcreAIII promoter with the CAT nucleotides inserted in front of the ATG to obtain a NdeI site. The vertical lines illustrate the inserted sequences to obtain the fungal-bacterial fusion promoters.

FIG. 3 shows the relevant parts of modified fungal promoters able to drive expression in prokaryotes. (A). the essential part of the *B. subtilis* PE4 promoter with the bacterial consensus elements underlined. (B). the relevant part of the three PpcbC variants: wild type (WT) and modified (INS and EXC) with the bacterial elements included underlined and all modifications with respect to the WT sequence in capitals. (C). the relevant part of the three PgpdA variants: wild type (WT) and modified (INS and EXC) with the bacterial elements included underlined and all modifications with respect to the WT sequence in capitals.

FIG. 4 shows the functioning of the PgpdA-INS and PgpdA-EXC promoters in *E. coli*. (A). shows the growth of the *E. coli* cells on agar plates with zeocin. (B). Legend, Pwt=WT gpdA promoter, Pins=gpdA-INS promoter, Pexc=gpdA-EXC promoter, neg='empty' *E. coli* cells.

FIG. 5 shows the promoter of Pc12g14840, a *Penicillium chrysogenum* polynucleotide control sequence following the formula I consensus sequence. (A). wt=wild type polynucleotide control sequence with essential elements underlined; CD1=variant polynucleotide control sequence of Pc12g14840 with CAT introduced to create a NdeI site; CD2=variant polynucleotide control sequence of Pc12g14840 with additionally a ribosome binding site introduced (underlined). The basepairs introduced are in capitals. (B). shows the growth of the *E. coli* cells with either CD1 of CD2 polynucleotide control sequences driving the transcription of the ble gene on agar plates with zeocin.

Figure 6:
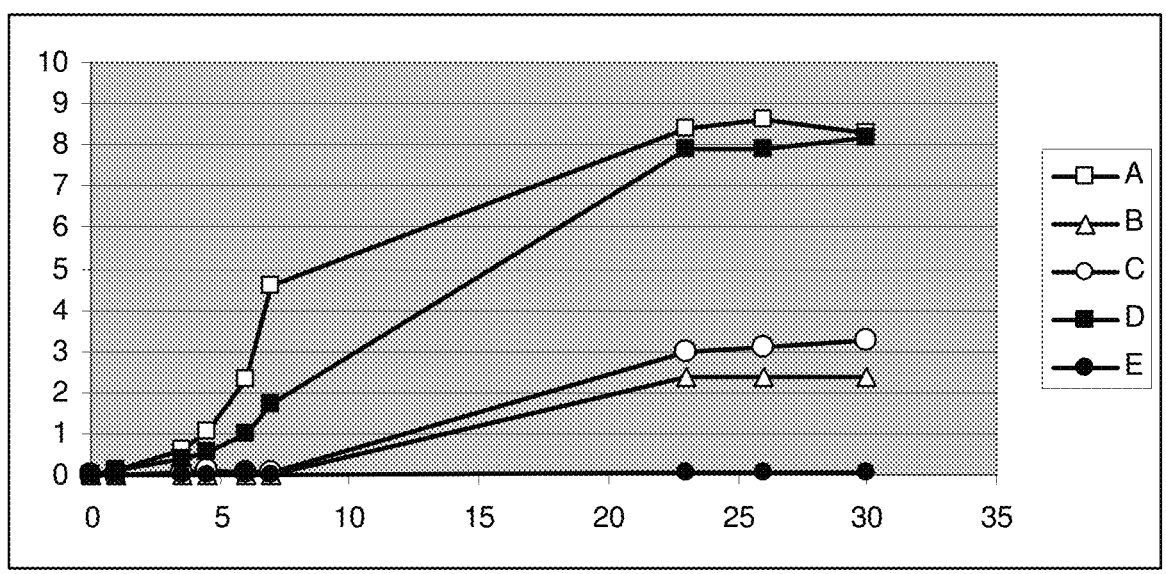

FIG. 6 shows the growth curves of RV308 with either pAnamdScA (open symbols) or pUC19 (closed symbols). Squares (A and D)=2×YT; Triangles (B)=AFM+Ammoniumchloride; Circles (C and E)=AFM+acetamide.

Figure 7:
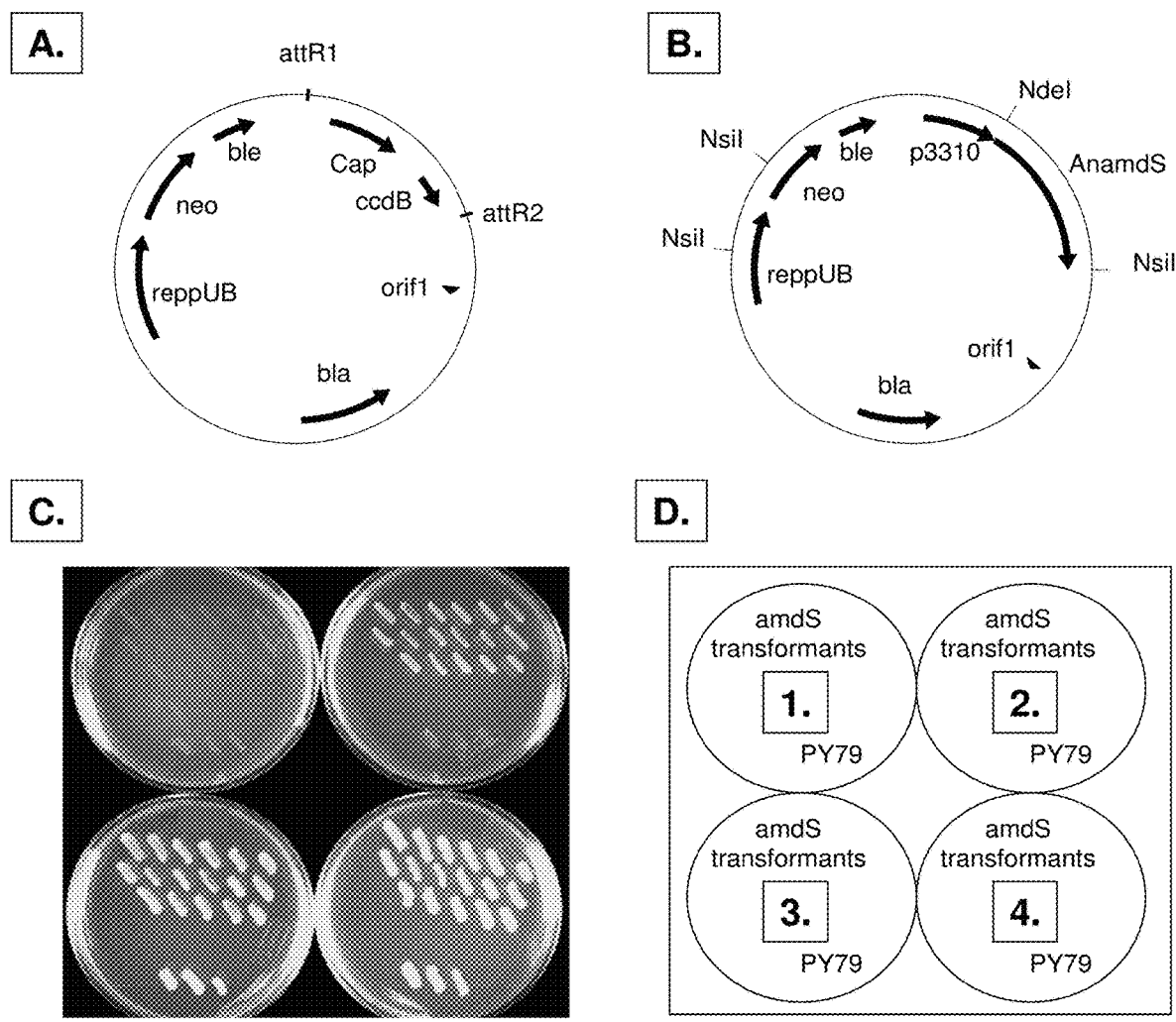

FIG. 7 shows the growth of *Bacillus subtilis* 1A747 after transformation with pBHA-3310amdS. (A). Plasmid map of pBHA12-DEST. (B). Plasmid map of pBHA-3310amdS. (C). Restreaked transformants on no N-source (plate 1, see panel D); acetamide (plate 2, see panel D), glutamine (plate 3, see panel D), glutamine+acetamide (plate 4, see panel D). (D). Legends for plates in panel C.

Figure 8:
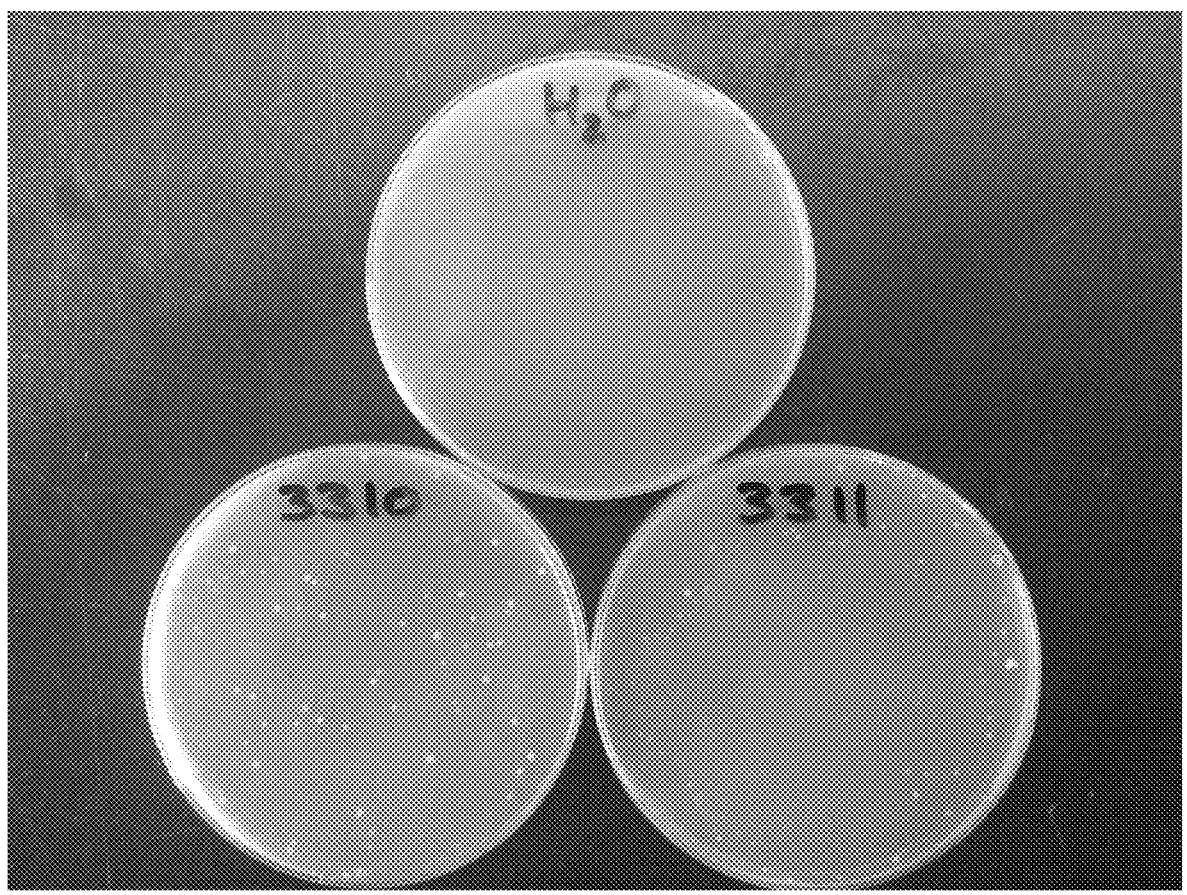

FIG. 8 shows the growth of *Saccharomyces cerevisiae* CEN.PK113-5D (Δura3) transformed with pYDEST-3310amdS and pYDEST-3311amdS. Legend: H20, CEN.PK113-5D transformed with water; 3310, CEN.PK113-5D transformed with pYDEST-3310amdS; 3310, CEN.PK113-5D transformed with pYDEST-3311amdS.

EXAMPLES

General Methods

In the Examples standard molecular techniques have been applied as described in literature (Sambrook et al., 1989, Molecular cloning: a laboratory manual", CSHL press, Cold Spring Harbour, N.Y.), unless stated otherwise.

Comparative Example 1

*Streptomyces griseus* Saf Promoter is not Functional in *Escherichia coli*

To test the usefulness of the bacterial saf promoter as a possible generic promoter the sequence was produced as synthetic DNA (Codon Devices, Cambridge, Mass., USA) controlling the expression of the ble gene, which encodes a protein mediating resistance against zeocin, bleomycin and phleomycin. SEQ ID NO. 52 was cloned in the EcoRI and BamHI sites of pUC19, transfected to the *E. coli* strain DH5alpha (Invitrogen) and selected on the presence of the bla gene, which is part of the vector backbone, in 2×YT+100 μg/ml ampicillin.

Ampicillin-resistant clones were restreaked on 2×YT+20 μg/ml zeocin and 2×YT+100 μg/ml ampicillin (control). Growth was only visible on the ampicillin plates, showing that in contrast what is reported by (Asturias et al., 1990) the saf promoter was not functional in *E. coli* with the ble gene and therefore not suitable for our purposes.

Comparative Example 2

The Fungal gpdA and pcbC Promoters are not Functional in *Escherichia coli*

To test the usefulness of the fungal gpdA and pcbC promoters as possible generic promoters, the sequences were produced as synthetic DNA (Codon Devices, Cambridge, Mass., USA) controlling the expression of the ble gene, which encodes a protein mediating resistance against zeocin, bleomycin and phleomycin.

Preparation of a Glucose-Repression Insensitive Variant of the *Penicillium chrysogenum* pcbC Promoter The pcbC gene of *Penicillium chrysogenum* is a strongly expressed gene but suffering from glucose repression (Gutiérrez et al., Microbiology 1999, 145:317-324). Repression may be deleted by the deletion of one or more creA sites. Therefore, first promoter variants were constructed in which three putative creA sites were deleted (see FIG. 1A for details). To this end first a control reporter construct was made: pEGPT12. In here the eGFP gene, encoding Green Fluorescent Protein, is under control of the pcbC promoter. To this end the eGFP gene was PCR amplified using the oligonucleotides of SEQ ID NO 53 and 54 from plasmid pEGFP-C1 (Clontech) using a proof reading enzyme (HiFi polymerase, Boehringer Mannheim) in a standard amplification program. Directly after the 30 PCR cycli 1 unit of AmpliTaq polymerase (PerkinElmer) was added to the reaction mixture and incubated for 30 min at 37° C. This introduced a 3'-adenine for efficient cloning in the pCR2.1 TOPO T/A vector (Invitrogen). The correct sequence was verified via sequencing. eGFP cloned into pCR2.1 yielded plasmid pEGFP7. The promoter (SEQ ID NO 65) and terminator regions of the pcbC gene were amplified as an 810 bp fragment using the oligonucleotides SEQ ID NO 55 plus 56 and as an 807 bp fragment using the oligonucleotides of SEQ ID NO 57 plus 58, respectively. Both were PCR amplified and cloned as described above in the pCR2.1 TOPO T/A vector. By this several restriction sites were introduced to facilitate further cloning steps: NarI, HpaI, EcoRV and ClaI (around the ATG) and NotI, ClaI, SalI and XbaI (in the terminator region). The promoter fragment was isolated as a NarI-ClaI fragment and cloned in the ClaI site of the terminator clone. The resulting promoter terminator cassette was digested with ClaI to ensure ligation of the eGFP ORF (isolated as a ClaI-NarI fragment), leading to the final plasmid pEGPT12 with eGFP under control of the *P. chrysogenum* pcbC promoter. The resulting eGFP expression cassette could be isolated from pEGPT12 as a 2.6 kb NotI fragment to be used for transformations to *Penicillium chrysogenum*.

To delete the first creA site a fusion PCR was performed. First, two individual PCR reactions were performed to amplify both left and right parts of the promoter, introducing an EcoRI site (GAATTC) at the site of the most upstream putative creA binding site (see FIG. 1A). This was done using the oligonucleotides of SEQ ID NO 55 plus 59 (amplifying the part of the promoter upstream to the creA site) and using the oligonucleotides of SEQ ID NO 60 plus 56 (amplifying the part of the promoter downstream to the creA site). The fragments were separated on an agarose gel, extracted from gel (QiaQuick Extraction kit, Qiagen) and together used as template for a fusion PCR reaction using the oligonucleotides of SEQ ID NO 55 plus 56. This fragment was cloned in pCR2.1 TOPO T/A and after sequence verification the NdeI-ClaI fragment was isolated and used to replace the WT promoter of pEGPT12, yielding a plasmid with eGFP under control of the PpcbC-creAI promoter (SEQ ID NO 66).

To delete the second and third putative creA sites first two individual PCR reactions were performed to amplify both left and right parts of the promoter with the PpcbC-creAI as a template, introducing a MunI site (CAATTG) at the site of the two putative creA binding site closest to the ATG. This was done using the oligonucleotides of SEQ ID NO 55 plus 61 (amplifying part of the promoter upstream of the $2^{nd}$ and $3^{rd}$ creA sites) and using the oligonucleotides of SEQ ID NO 62 plus 56 (amplifying part of the promoter downstream of the $2^{nd}$ and $3^{rd}$ creA sites). Both fragments were cloned separately in pCR2.1 TOPO T/A and after sequence verification both were isolated via NdeI-MunI (5' part) and MunI-ClaI (3' part). After ligation with the pEGPT12 digested with NdeI-ClaI, the final plasmid with all three creA sites deleted was obtained: a plasmid with eGFP under control of the PpcbC-creAIII promoter (SEQ ID NO 67).

Both the WT and the ΔcreAIII promoter variant eGFP expression constructs were isolated from the plasmid backbone by NotI digestion and used to transform *P. chrysogenum*. Techniques involved in the transfer of DNA to protoplasts of *Penicillium chrysogenum* are well known in the art and are described in many references, including Finkelstein and Ball (eds.), Biotechnology of filamentous fungi, technology and products, Butterworth-Heinemann (1992); Bennett and Lasure (eds.) More Gene Manipulations in fungi, Academic Press (1991); Turner, in: Pühler (ed), Biotechnology, 2$^{nd}$ completely revised edition, VHC (1992). The Ca-PEG mediated protoplast transformation is used as described in EP 635,574. The amdS expression construct from pHELY-A1 (described in WO04/106347) was used as for co-transformation. Two µg of PpcbC-WT-EGFP and PpcbC-ΔcreAIII-EGFP were transformed to *P. chrysogenum* (with 0.25 µg of the amdS expression construct). Transformants were selected on media with acetamide as the sole nitrogen source. To secure obtaining stable transformants, first round positives were colony purified on fresh acetamide plates and subsequently transferred to non-selective, rich media (YEPD) to induce sporulation. Afterwards all colonies were again tested on acetamide media.

Spores of stable amdS transformants were used to inoculate liquid media. One of the media was essentially the same as described by De Laat et al. (US 2002/0039758). In the other all lactose was replaced by glucose, being the sole carbon source. Samples were taken after 4 days of growth (at 25 degrees C. and 280 rpm). Total RNA was isolated from approximately 10$^6$ cells using the StrataPrep Total RNA MicroPrep Kit (Stratagene). One-tenth of the total RNA was used for oligo-dT directed cDNA synthesis (Thermoscript RT-PCR, Life Technologies), which was used as template for 30 cycles of PCR (SuperTaq by Enzyme Technologies, UK) using the specific oligonucleotides SEQ ID NO 63 and 64. As can be seen by comparing FIGS. 1B and 1C, the deletion of the creA sites abolishes the glucose repression of the pcbC promoter completely.

Testing the Functionality of the Fungal gpdA and pcbC Promoters in *Escherichia coli*

The glucose-repression-insensitive variant of pcbC promoter of *Penicillium chrysogenum* as described above (pcb-CΔcreAIII, SEQ ID NO 67) and the gpdA promoter of *Aspergillus nidulans* were tested for driving expression in *E. coli*. However, for convenience of further cloning, in the glucose-repression-insensitive variant of the pcbC promoter, the HpaI site was omitted and an NdeI site was introduced directly in front of the ATG. Both constructs were made synthetically in front of the ble gene (DNA2.0, Menlo Park, Calif. 94025, USA) and with a fungal terminator sequence. These two polynucleotides (promoter-ble gene-terminator) of SEQ ID NO 68 and 70 were cloned in the pDONR221 vector of Invitrogen via a Gateway reaction (see for manuals: www.invitrogen.com) and correct clones were obtained after kanamycin selection (respectively p3305ble and p3309ble).

Kanamycin-resistant clones were re-streaked on 2×YT+ 20 µg/ml zeocin and 2×YT+50 µg/ml kanamycin (control). Growth was only visible on the kanamycin plates, indicating that the observation by Hamer et al. (2001, Proc Natl Acad Sci USA 98: 5110-5115), who describe the use of the fungal trpC promoter with the hph gene (resistance against hygromycinC) in *E. coli* is not generally applicable. Our results indicate that the examples in literature are very specific for the cases described and the methodologies are not generally applicable.

To verify the functioning in fungi, both ble expression cassettes were transformed to *P. chrysogenum* protoplasts as described above and plated out on agar plates (YEPD+1.0 M Saccharose) with 50 µg/ml phleomycin. As both experiments yielded phleomycin resistant transformants it was clear that the synthetic nature had not changed their functioning as fungal promoters.

Comparative Example 3

Fungal-Bacterial Fusion Promoters are not Active in *Escherichia coli*

In a next attempt to engineer a promoter which is active in both eukaryotes and prokaryotes, the fusion methodology was used. In this method a prokaryotic promoter is inserted between the full eukaryotic promoter and the eukaryotic start codon ATG. We used two widely used and strong fungal promoters, viz. the pcbC promoter of *Penicillium chrysogenum* and the gpdA promoter of *Aspergillus nidulans*.

The glucose-repression-insensitive variant of pcbC promoter of *Penicillium chrysogenum* as prepared in Example 2 (pcbCΔcreAIII, SEQ ID NO 67), and the gpdA promoter of *Aspergillus nidulans* were tested in the fusion methodology.

The PE4 promoter of *Bacillus subtilis* (Stewart et al., 1998, Virology 246: 329-340) was selected as a strong prokaryotic promoter with all the known consensus elements of a prokaryotic promoter. The last 84 bases of this promoter, which contain all the essential promoter elements, were inserted between the fungal promoters and the ATG startcodon (see FIG. 2 for details). Both constructs were made synthetically in front of the ble gene (DNA2.0, Menlo Park, Calif. 94025, USA) and with a fungal terminator sequence. These two polynucleotides (promoter-b/e gene-terminator) of SEQ ID NO 69 and 71 were cloned in the pDONR221 vector of Invitrogen via a Gateway reaction (see for manuals: www.invitrogen.com) and correct clones were obtained after kanamycin selection (respectively p3308ble and p3312ble).

Kanamycin-resistant clones were re-streaked on 2×YT+ 20 µg/ml zeocin and 2×YT+50 µg/ml kanamycin (control). Growth was only visible on the kanamycin plates, showing that simply fusing the eukaryotic and prokaryotic promoters was not yielding functional *E. coli* promoters when applied to fungal promoters like pcbC and gpdA (SEQ ID NO 69 and 71).

To verify the functioning in fungi, both ble expression cassettes were transformed to *P. chrysogenum* protoplasts as described in Example 2 and plated out on agar plates (YEPD+1.0 M Saccharose) with 50 µg/ml phleomycin. As both experiments gave phleomycin resistant transformants it was clear that the synthetic nature had not changed their functioning as fungal promoters. Moreover, the insertion of a bacterial promoter did not disturb fungal promoter activity.

Example 4

Multisite Insertion of Bacterial Sequences in Fungal Promoters Drive Efficient Gene Expression in *Escherichia coli*

In a further attempt to find a promoter which is active in both eukaryotes and prokaryotes, consensus sequences in the last 84 basepairs of the PE4 promoter of *Bacillus subtilis* (Stewart et al., 1998) were inserted at several positions in the glucose-repression-insensitive pcbC promoter of *Penicillium chrysogenum* (SEQ ID NO 67) and in the gpdA promoter of *Aspergillus* (SEQ ID NO 70). This lead to the polynucleotide sequences of SEQ ID NO 46 and 48, respectively, embedded in the polynucleotide control sequences of SEQ ID No 72 and 74. All constructs were made synthetically in front of the ble gene (DNA2.0, Menlo Park, Calif. 94025, USA) followed by fungal terminators (yielding plasmids p3306ble and p3310ble, respectively). In some cases the bacterial sequences replaced the fungal sequences at the site of insertion. This lead to the polynucleotide sequences of SEQ ID NO 47 and 49, respectively, embedded in the polynucleotide control sequences of SEQ ID No 73 and 75 (i.e. an exchange of sequences, yielding plasmids p3307ble and p3311ble, respectively).

Polynucleotides were cloned in the pDONR221 vector of Invitrogen via a Gateway reaction (see for manuals: www-.invitrogen.com) and correct clones were obtained after kanamycin selection. Kanamycin-resistant clones were re-streaked on 2×YT+20 µg/ml zeocin and 2×YT+50 µg/ml kanamycin (control). As controls the two non-adapted fungal promoters were used (see Example 2, p3305ble and p3309ble, SED ID NO 68 and 70). Good growth was visible on both selection plates with variants derived from both fungal promoters (see for example FIG. 4), in contrast to the non-modified fungal promoters, which only grew properly on the kanamycin plates.

Sequencing showed that positive results were obtained only with clones which comprised the following consensus sequence in their promoter (FIG. 3 and SEQ ID NO. 1 to 45):

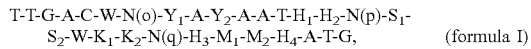

(formula I)

wherein,
N can be any of the nucleotides A, C, G and T, and N(o) is between 16 and 18 nucleotides long; N(p) is between 21 and 23 nucleotides long; N(q) is between 2 and 6 nucleotides long and all N may be the same or different;
W can be any of the nucleotides A and T, and all W may be the same or different;
Y can be any of the nucleotides C and T, and all Y may be the same or different;
H can be any of the nucleotides A, C, and T and all H may be the same or different;
S can be any of the nucleotides G and C, and all S may be the same or different;
K can be any of the nucleotides G and T, and all K may be the same or different;
M can be any of the nucleotides A and C, and all M may be the same or different;
The AG-content of N(o) is below 50%
The A-content of N(o) is below 35%
The AG-content within each stretch of 6 nucleotides in N(o) is below 66%
The AG-content of N(p) is below 60%
The AG-content within each stretch of 6 nucleotides in N(p) is below 83%
N(o) and N(p) do not contain two consecutive G's
The G-content of N(q) is below 50%.

To verify the functioning in fungi, the various ble expression cassettes actively transcribed in *E. coli*, were transformed to *P. chrysogenum* protoplasts as described in Example 2 and plated out on agar plates (YEPD+1.0 M Saccharose) with 50 µg/ml phleomycin. As all experiments gave phleomycin resistant transformants it was clear that the synthetic nature had not changed their functioning as fungal promoters. Moreover, the insertion of a bacterial promoter did not disturb fungal promoter activity.

So, surprisingly we found several polynucleotide control sequences which are active promoters in both eukaryotes and prokaryotes. The parent promoters are from different fungal origin and of different metabolic pathways (i.e. primary and secondary metabolism, respectively) showing that commonly used fungal promoters can be adapted to function in *E. coli*.

Example 5

Fungal Sterol Transmethylase Like Promoter Drives Expression in *E. coli*

To verify the general applicability of the consensus sequence, the genomic sequences of *Aspergillus niger* and *Penicillium chrysogenum* were screened for promoter regions which followed the consensus sequence of Example 4 and could be used in *E. coli*.

As an example, one promoter of *Penicillium chrysogenum* was identified that was actively transcribed under standard growth conditions (verified by Affymetrix MicroArrays) and followed the consensus sequence (see FIG. 5A). The promoter is in front of a gene with strong similarity to the sterol transmethylase ERG6 of *Candida albicans*. Two constructs were made synthetically in front of the ble gene (Codon Devices, Cambridge, Mass., USA) and followed by termination sequences. One synthetic construct contains one modification in the promoter sequence: CAT in front of the startcodon to introduce an NdeI site (the polynucleotide sequence of SEQ ID NO 50, embedded in the polynucleotide control sequence of SEQ ID NO 76). The other synthetic construct contains besides this CAT a second modification in the promoter sequence: an inserted Ribosome Binding Site (RBS; the polynucleotide sequence of SEQ ID NO 51, embedded in the polynucleotide control sequence of SEQ ID NO 77). The two polynucleotides of SEQ ID NO 76 and 77 (promoter-b/e gene-terminator) were cloned between the EcoRI and BamHI sites of pUC19 and correct clones were obtained after ampicillin selection.

Ampicillin-resistant clones were re-streaked on 2×YT+20 µg/ml zeocin and 2×YT+100 µg/ml ampicillin (control). Growth was visible for both constructs on the zeocin plates (FIG. 5B), demonstrating that the polynucleotide control sequences following the consensus sequence are active both in fungi and in *E. coli*.

This polynucleotide control sequence is just one example; with the availability of various genome sequences one could use in silico screening to rapidly identify substantially homologous polynucleotide control sequences and test these in suitable species.

Example 6

Use of the amdS Gene and Acetamide Selection in *Escherichia coli*

As the amdS gene encoding acetamidase (for example the *Aspergillus nidulans* amdS gene), is a useful selectable marker gene in yeast and fungi from which transformants can be readily selected for the presence or the absence, it would be very useful if such a marker would function in prokaryotes, as they are often incapable of growing on acetamide (see for example the results below) and the gene is not part of general metabolism. To this end the cDNA of the *Aspergillus nidulans* amdS gene was PCR amplified from mRNA isolated from amdS positive *Penicillium* transformants of Example 2. Total RNA was isolated from approximately $10^6$ cells using the StrataPrep Total RNA MicroPrep Kit (Stratagene). One-tenth of the total RNA was used for oligo-dT directed cDNA synthesis (Thermoscript RT-PCR, Life Technologies), which was used as template for 30 cycles of PCR (using a proofreading enzyme) using the specific oligonucleotides SEQ ID NO 78 and 79. Directly after the 30 PCR cycli 1 unit of AmpliTaq polymerase (PerkinElmer) was added to the reaction mixture and incubated for 30 min at 37° C. This introduced a 3'-adenine for efficient cloning in the pCR2.1 TOPO T/A vector (Invitrogen). The correct sequence was verified via sequencing. Afterwards the NdeI-NsiI fragment was recloned in the same sites in plasmid pISEWAn (WO04/106347). Next, the fungal PpcbC promoter, which does not drive proper expression in *E. coli* (see Example 3), was exchanged for the promoter of the bla gene, mediating resistance to ampicillin, as being present on commercial plasmids. To this end the promoter was PCR amplified from plasmid backbone using the specific oligonucleotides SEQ ID NO 80 and 81. After cloning in pCR2.1 TOPO T/A vector (Invitrogen), the EcoRI-NdeI fragment was isolated and used to exchange for the PpcbC, yielding pAnamdScA (i.e. the *Aspergillus nidulans* amdS gene under control of the bla promoter). The construct was transformed to RV308 (ATCC31608) and transformants were obtained on 2×YT+100 µg/ml ampicillin. As a control pUC19 was transformed to the same strain. Transformants were inoculated in liquid rich medium (2×YT) or liquid mineral medium (AFM: 50 mM $K_2HPO_4$, 4 mM citric acid, 1 mM $MgSO_4$, 3 mM $FeCl_3$, 1 mM $MnCl_2$, 1 mM $CaCl_2$, 2 g/l glucose, with either 20 mM $NH_4Cl$ or 1 g/l acetamide as nitrogen source) and cultivated at 25 degrees C. and 280 rpm. As can be seen in FIG. 6 RV308 with pAnamdScA can readily grow on acetamide; even better as on ammonium. Upon the availability of these results direct selection on acetamide was tried. After electroporation with pAnamdScA, RV308 was regenerated in 1 ml of AFM+1 g/l acetamide and incubated for 1 hour at 25 degrees C. and subsequently plated on AFM+1 g/l acetamide agar plates. After 3 days colonies appeared and 7 were restreaked on 2×YT+100 mg/ml ampicillin. From these plates they were inoculated in liquid AFM+acetamide and plasmids were isolated after 2 days of growth at 25 degrees C. and 280 rpm. The restriction patterns of all plasmids matched that of pAnamdScA exactly, demonstrating that direct selection on acetamide with the fungal amdS gene in *E. coli* is possible.

Example 7

Synthetic Polynucleotide Control Sequences Drive Efficient Acetamide Selection in *Escherichia coli*

As shown in Example 6 the amdS gene under control of a typical prokaryotic promoter can be used to select readily growing transformants in *E. coli*. It would be extremely useful if the acetamide based selection using the amdS gene would work in combination with the modified synthetic polynucleotide control sequences which were shown to operate in both fungi and *E. coli* (see Example 4). In that case the same expression cassette with both forward and reverse selection (on acetamide and fluoroacetamide, respectively) could be used in multiple species, reducing cloning steps while switching from species to species. To this end the ble gene was removed from plasmids p3310ble and p3311ble (see Example 4) via a NdeI-NsiI digest and replaced by the cDNA of amdS isolated as NdeI-NsiI fragment of pAnamdScA (see Example 6), resulting in p3310amdS and p3311amdS, respectively. The transformation mixtures (obtained by transforming the ligation mixture to RV308) were directly plated out on AFM+1 g/l acetamide. After three days at 25 degrees C. colonies were obtained on the agar plates, while no colonies appeared on the control plate.

So, surprisingly the polynucleotide control sequences of the present invention in combination with selection marker genes like amdS provide for a very efficient selection marker cassette which can be used in a wide range of industrial relevant species.

Example 8

Synthetic Polynucleotide Control Sequences Drive Efficient Gene Expression in *Penicillium chrysogenum*

To test if the synthetic polynucleotide control sequences of Examples 3 and 4 also drive transcription in fungi, all contructs (p3305ble, p3306ble, p3307ble, p3308ble, p3309ble, p3310ble, p3311ble and p3312ble) were transformed to *Penicillium chrysogenum* protoplasts. Techniques involved in the transfer of DNA to protoplasts of *Penicillium chrysogenum* are well known in the art and are described in many references, including Finkelstein and Ball (eds.), Biotechnology of filamentous fungi, technology and products, Butterworth-Heinemann (1992); Bennett and Lasure (eds.) More Gene Manipulations in fungi, Academic Press (1991); Turner, in: Pühler (ed), Biotechnology, $2^{nd}$ completely revised edition, VHC (1992). The Ca-PEG mediated protoplast transformation is used as described in EP 0 635 574. One µg of each plasmid was transformed to *P. chrysogenum* and transformants were selected on 0.5×YEPD with 1.0 M saccharose and 50 µg/ml phleomycin. With each construct many transformants were obtained (between 20 and 1000), while after transformation with water no phleomycin resistant colonies were obtained. So, the synthetic polynucleotide control sequences active in *E. coli* are also active in *P. chrysogenum*.

Example 9

Synthetic Polynucleotide Control Sequences Drive Efficient Gene Expression in *Bacillus subtilis*

To test if the synthetic polynucleotide control sequences of Examples 3 and 4 drive transcription in bacilli, selected constructs (p3310amdS and p3311amdS, see Example 7) were transferred to a *Bacillus* vector (pBHA12-DEST) via a Gateway reaction. pBHA12-DEST was obtained by insertion of the attR1-cat/ccdB-attR2 cassette in the pBHA12 vector (WO2008/000632). To obtain pBHA12-DEST, the attR1-cat/ccdB-attR2 cassette was PCR amplified from pDEST15 (Invitrogen) using the oligonucleotides of SEQ ID NO 82 and 83 and cloned after BpiI digestion in the BamHI-NotI sites of pNHA12, yielding pBHA12-DEST. Ampicillin resistant colonies of TOP10 (Invitrogen) obtained after the Gateway reactions were cultivated, plasmids isolated and verified via restriction analysis. For both clones the *Bacillus*-variant vector was obtained (named respectively, pBHA-3310amdS and pBHA-3311amdS). Both plasmids were transformed to JM110 to isolate dam-methylase negative DNA which should be used for *B. subtilis* transformations.

*B. subtilis* 1A747 (*Bacillus* Genetic Stock Center, The Ohio State University, Columbus, Ohio 43210 USA) was chosen as host strain for the transformation experiments. Basic medium was BFA-N with either no N-source, or glutamine (0.2%) and/or actemide (0.1%). BFA-N(per liter) contains $K_2SO_4$, 11.5 mM; $K_2HPO_4$.5 $H_2O$, 62 mM; $KH_2PO_4$, 44 mM; sodium citrate.$7H_2O$, 3.4 mM; magnesium sulfate.$7H_2O$, 0.8 mM; glucose, 4 g; $FeCl_3$, 4 mg; $MnSO_4$.$7H_2O$, 0.2 mg; $CaCl_2$, 5.5 mg; $ZnCl_2$, 1.7 mg; $CuCl_2$.$2H_2O$, 0.43 mg; $CoCl_2$.$6H_2O$, 0.6 mg; $Na_2MoO_4$.$2H_2O$, 0.6 mg. On the acetamide version of this medium *B. subtilis* 1A747 cannot grow (see FIG. 7). One µg of pBHA-3310amdS and pBHA-3311amdS were transformed to *B. subtilis* 1A747. Transformants were selected on LB plates with 12.5 µg/ml kanamycin: 17 with pBHA-3310amdS and 190 with pBHA-3311amdS. The 17 transformants of pBHA-3310amdS were restreaked on BFA-N agar plates with either no N-source, or glutamine (0.2%), or acetamide (0.1%), or glutamine (0.2%) and acetamide (0.1%). As can be seen in FIG. 7 *B. subtilis* 1A747 with pBHA-3310amdS can grow very well on acetamide, while *B. subtilis* 1A747 cannot. For pBHA-3311amdS a similar result was obtained although the growth rate was slower Next a direct acetamide selection after transformation was tried. This only worked with concurrent kanamycin selection.

In conclusion, very surprisingly all promoters tested did function in *B. subtilis*. Therefore, the synthetic polynucleotide control sequences active in a gram-negative species as *E. coli* and a fungus as *P. chrysogenum* are also active in a gram-positive species as *B. subtilis*.

Example 10

Synthetic Polynucleotide Control Sequences Drive Efficient Gene Expression in *Saccharomyces cerevisiae*

To test if the synthetic polynucleotide control sequences of Examples 3 and 4 drive transcription in yeasts, selected constructs (p3305ble, p3306ble, p3307ble, p3309ble, p3310 ble, p3311ble, p3310amdS and p3311amdS; see Examples 3, 4 and 7) were transferred to a yeast vector (pYES-DEST52) via a Gateway reaction. Ampicillin resistant colonies were cultivated, plasmids isolated and verified via restriction analysis. For all clones the yeast-variant vector was obtained (respectively, pYDEST-3305ble, pYDEST-3306ble, pYDEST-3310ble, pYDEST-3311ble, pYDEST-3310amdS and pYDEST-3311amdS).

*Saccharomyces cerevisiae* CEN.PK113-5D (Δura3) was pre-grown overnight in liquid YEPD, 30 C and 280 rpm. The culture was 10-fold diluted to an $OD_{600}$ of 0.4 (approximately $1 \times 10^6$ cells/ml). Cells were made competent using the Fast-Yeast transformationkit of Genotech. Twenty ml of the culture was spun down; the pellet was washed with 20 ml of washbuffer and finally resuspended in 2 ml competency buffer. To fifty µl of this cell suspension 5 µl of DNA (~1 µg) or water was added, and 500 µl transformation solution. The cells for selection on mineral media were plated after 45 minutes incubation at 30 C, while to the other mixtures 1 ml of YEPD was added for a prolonged incubation of 3 hours to induce the expression of the ble gene before plating out on phleomycin plates (see for details Table 1).

Surprisingly, as can be seen in Table 1 all plasmids with a ble gene gave phleomycin resistant yeast colonies and all plasmids with the amdS gene gave acetamide consuming yeast colonies (see also FIG. 8), with the expression driven by the synthetic polynucleotide control sequences. As control, colonies from the MM selection plates were used to make dilutions which were spotted on phleomycin or acetamide selective plates. In all cases the results of the direct selections were confirmed.

TABLE 1

Details *Saccharomyces cerevisiae* transformations

| Transformation | YF* | MM* | FA# |
|---|---|---|---|
| Water | 0 | 0 | 0 |
| pYDEST-3305ble | 1 | ~200 | n.t. |
| pYDEST-3306ble | 3 | ~150 | n.t. |
| pYDEST-3310ble | 4 | ~200 | n.t. |
| pYDEST-3311ble | 1 | ~200 | n.t. |
| pYDEST-3310amdS | 0 | ~100 | ~100 |
| pYDEST-3311amdS | 0 | ~200 | ~50 |

YF = YEPD + 20 µg/ml phleomycin;
MM = in g/l: agar, 15; Yeast Nitrogen Base, 6.7; glucose, 20;
FA = acetamide selection medium according to WO97/06261;
n.t. = not tested;
* = transformants after 4 days;
# = transformants after 11 days So, surprisingly all synthetic polynucleotide control sequences tested did function in *S. cerevisiae*. Therefore, the synthetic polynucleotide control sequences active in a gram-negative species as *E. coli*, in a fungus as *P. chrysogenum* and a gram-positive species as *B. subtilis* are also active in yeasts as *S. cerevisiae*.

Example 11

Using the *Aspergillus nidulans* amdS Gene as a Trap in *P. chrysogenum* for New Polynucleotide Control Sequences To identify new polynucleotide control sequences a 'trap' with the multifunctional *A. nidulans* amdS cDNA (see Examples 6, 7 and 10) was set-up. To this end the *A. nidulans* amdS cDNA was PCR amplified as described in Example 6, but with the oligonucleotides of SEQ ID NO 84 and 85 to introduce NdeI, BstBI and NsiI sites for subsequent re-cloning steps. The PCR fragment was cloned in pCR2.1 TOPO T/A and sequence verified. Afterwards the NdeI-NsiI fragment was recloned in the same sites in plasmid pISEWAn (WO04106347), to obtain plAnamdScA. Next, the fungal pcbC promoter of this vector was replaced by putative polynucleotide control sequences. To this end putative polynucleotide control sequences were PCR amplified using *P. chrysogenum* chrosomomal DNA as template with the oligonucleotides of SEQ ID NO 86 and 87. SEQ ID NO 87 spans the amdS ATG startcodon, preceded by four A or C's as in SEQ ID NO. 1 to 45; followed by a ClaI restriction site to enable in-frame cloning on the BstBI site in the amdS gene. The fragments of these PCR-reactions were pooled and cloned into the pCR2.1 TOPO T/A vector. The introduction of the fragments into the vector was verified by restriction analysis: restriction with ClaI and SmaI gave a collection of bands, indicative for a range of fragments. The mixture of putative polynucleotide control sequences was isolated via EcoRI (originating from the pCR2.1 vector) and ClaI digestion and cloned in the EcoRI-BstBI sites of plAnamdScA, leading to a library of plasmids labelled pXAnamdScA. This library was transformed to *P. chrysogenum* protoplasts and amdS positive transformants were selected as described in Example 2. Thirty-seven colonies were restreaked on fresh acetamide plates and subsequently transferred to YEPD plates to induce sporulation. From there single colonies were used to inoculate liquid acetamide media (in 25 ml, at 25 degrees C. and 280 rpm) and good growing cultures were selected to isolate chromosomal DNA. These were used as template for PCR reactions with Supertaq polymerase using the oligonucleotides of SEQ ID NO 88 and 89 (respectively, the M13 reverse primer and an internal primer of amdS). Fragments obtained were cloned in pCR2.1 TOPO T/A and transformed to TOP10F E. coli cells (Invitrogen). One-hundred-twenty-two colonies were selected for plasmid isolation and 33 of these were selected (based on restriction analysis) for sequencing. This led to the identification of 10 unique polynucleotide control sequences (SEQ ID NO 90 to 99) which drive transcription in P. chrysogenum. These can be tested in other (i.e. second host) species to further select the specific polynucleotide control sequences active in multiple species. This Example is just meant as an illustration. The one trained in the art understands that by selecting more initial transformants, using other donor DNA for the first PCR reaction or using other first host species the one can identify other polynucleotide control sequences.

Example 12

Using the Ble Gene as a Trap for Nucleic Acid Sequences with Multi-Species Promoter Activity To identify new polynucleotide control sequences a 'trap' with the multifunctional ble gene (see Examples 4, 8, 9 and 10) was set-up. Chromosomal DNA was isolated from 6 different species: Taxus baccata, Streptomyces coelicolor, Penicillium chrysogenum, Acremonium chrysogenum, Penicillium nalgiovense and Neurospora crassa with the standard phenol:chloroform method.

The wild type gpdA polynucleotide control sequence construct of Aspergillus nidulans which does not properly function in E. coli (SEQ ID NO 70, p3309ble, see Example 3) was used as a cloning vector. To this end the promoter was precisely deleted via digestion with SphI and NdeI, resulting in a linear fragment. All genomic DNA samples were also digested with NdeI and SphI. After digestion all samples were purified (Qiagen PCR purification Columns). Ligation was done using 30 ng of digested vector and 300-1000 ng digested chromosomal DNA. After transformation to DH10alpha electromax cells (Invitrogen), between 9 and 400 colonies were obtained (depending on the chromosomal DNA donor) while directly selecting for zeocin resistance. All colonies appearing must have a fragment of DNA functioning as a promoter.

Plasmids isolated can be used to transform as second species, for example P. chrysogenum. The plasmids that give phleomycin resistant Penicillium transformants are selected for testing in Saccharomyces cerevisiae. To this end a DEST reaction will be performed (as described in Example 10). The resulting DEST clones can be transformed to yeast (described in Example 10). All uracil positive clones are re-streaked on phleomycin selective plates. All phleomycin resistant colonies are used to isolate plasmid DNA and re-transform E. coli. All plasmids are isolated from E. coli transformants and new multi-species promoter sequences are determined. Also, the original host can be identified (if necessary) via nucleic acid hybridization.

Example 13

Using Multi-Species Active Polynucleotide Control Sequences to Enhance the Selectivity of Multi-Site Gateway DEST Reactions Gateway DEST reactions are meant to recombine more than one fragment into a new vector (typically 2-5 fragments, see Invitrogen.com) without the use of restriction enzyme digestion and ligation. However, these reactions are not 100% efficient and false positives can be obtained. Some conditions (for example long fragments, high GC contents, presence of repeats) can lead to a low number of correct clones; even leading to rates as low as 22% (see below). It is not surprisingly that this is unwanted. Especially in High Throughput projects as genome-wide knock-out libraries using linear DNA fragments for Double Homologous Recombination (=DHR) with a typical architecture like: left flank of g.o.i.—selection marker—right flank g.o.i. In such projects initial cloning steps are performed in laboratory workhorses like E. coli or S. cerevisiae which enable high throughput and relatively efficient construction of DNA fragments needed to transform the final host. For this one needs a highly efficient technology which is robust irrespective of for example the length of the substrate DNA or the GC content of the substrate DNA. As with 50% efficiency one already needs to analyze 2-4 clones per reaction to identify the correct one, adding 200-400% in cost and time. Ideally, the expression cassette for the selection marker used in the fragment for the DHR works both in the workhorse for cloning (yeast or E. coli) and in the final host (wherein the DHR needs to take place). Surprisingly, we found that the polynucleotide control sequences of the present invention in combination with a selection marker enables a 100% efficiency in a so-called multisite (MS) Gateway recombination reaction, when p3310ble was recombined with two sets of fragments (one with 50% GC and one set with 57% GC plus promoter features).

Multisite Gateway Reaction with 50% GC Fragments

The left flank of the Penicillium chrysogenum niaD gene was PCR amplified using the oligonucleotides SEQ ID NO 100 plus 101 and recombined in the pDONRP4-P1R Gateway ENTRY vector, yielding pDONR:niaDL. The right flank of the Penicillium chrysogenum niaD gene was PCR amplified using the oligonucleotides SEQ ID NO 102 plus 103 and recombined in the pDONRP2R-P3 Gateway ENTRY vector, yielding pDONR:niaDR. All three fragments for the multisite reaction were PCR amplified using Phusion polymerase (Finnzymes) from the DONR plasmids (pDONR:niaDL, p3310ble and pDONR:niaDR) using the standard M13 forward and reverse primers (see Invitrogen.com). The fragments were purified (Qiagen, QiaQuick kit) and used in a multisite reaction with the standard Destination vector pDESTR4-R3 and LR clonase Plus according to the suppliers instructions (Invitrogen). After overnight incubation at 16 C a part of the mixture was transformed to DH10α cells and plated on 2×YT+100 μg/ml ampicillin and 2×YT+100 μg/ml ampicillin+20 μg/ml zeocin. All colonies appearing were checked for antibiotic resistance and plasmids were isolate for restriction enzyme analyses. The results presented in Table 2 show that the selection pressure via the polynucleotide control sequences of the present invention increase the efficiency of the multisite gateway reaction from 76 to 100%.

TABLE 2

Multisite Gateway reaction with 50% GC

| MS Reaction | Cfu's on 2xYT | | Restreak to check for antibiotics on 2xYT | Correct plasmids |
|---|---|---|---|---|
| | +Amp | +Amp + Zeo | +Amp + Zeo | |
| niaDL-3310ble-niaDR | 37 | n.p. | 28 | 75.6% |

TABLE 2-continued

Multisite Gateway reaction with 50% GC

| MS Reaction | Cfu's on 2xYT | | Restreak to check for antibiotics on 2xYT | Correct plasmids |
|---|---|---|---|---|
| | +Amp | +Amp + Zeo | +Amp + Zeo | |
| niaDL-3310ble-niaDR | n.p. | 24 | 24 | 100% | n.p. = not plated out

Multisite Gateway Reaction with 57% GC Fragments

As left and right partners of the MS reaction two synthetic DNA fragments encoding a *Streptomyces* p450 enzyme and p450 reductase, respectively, were used. Both synthetic DNA fragments had not only higher GC contents than the niaD fragments as tested above, but also contained a promoter region with some smaller repeats. The synthetic DNA fragments (SEQ ID No 104 and 105) were directly cloned in the Gateway ENTRY vectors pDONRP4-P1R and pDONRP2R-P3, respectively. All three plasmids for the multisite reaction were used in a multisite reaction with the standard Destination vector pDESTR4-R3 and LR clonase Plus according to the suppliers instructions (Invitrogen). After overnight incubation at 16 C a part of the mixture was transformed to DH10α cells and plated on 2xYT+100 µg/ml ampicillin. All colonies appearing were checked for antibiotic resistance on 2xYT+100 µg/ml ampicillin+20 µg/ml zeocin and plasmids were isolated for restriction enzyme analyses. The results presented in Table 3 show that the selection pressure via the polynucleotide control sequences of the present invention increases the efficiency of the multisite gateway reaction from 22 to 100%.

TABLE 3

Multisite Gateway reaction with 57% GC

| MS Reaction | Cfu's on 2xYT + Amp | Restreak to check for antibiotics on 2xYT + Amp + Zeo | Correct plasmids after selection on | |
|---|---|---|---|---|
| | | | 2xYT + Amp | 2xYT + Amp + Zeo |
| p450-3310ble-RED | 18 | 2 | 22.2% | 100% |

Example 14

Using Multi-Species Active Polynucleotide Control Sequences to Enable Multiple Fragment STABY Cloning STABY cloning (Eurogentec) is based on the complementation of the ccdA antagonist of the toxic ccdB-gene product. Although a very efficient technology, it is limited to the cloning of a single fragment as there is only one inactive ccdA-gene to complement. Surprisingly, we found that the polynucleotide control sequences of the present invention in combination with a selection marker gene enables the 100% efficient cloning of three fragments in on reaction using the STABY technology.

Again we tried to make a fragment for a typical Double Homologous Recombination (=DHR) with an architecture like: left flank of g.o.i.—selection marker—right flank g.o.i. As left flank the promoter of the *Penicillium chrysogenum* niaD gene was PCR amplified using the oligonucleotides SEQ ID NO 106 plus 107 and digested with NcoI. As right flank the *Penicillium chrysogenum* niaD gene was PCR amplified using the oligonucleotides SEQ ID NO 108 plus 109 and digested with SalI. p3310ble was digested with NcoI and SalI. All fragments were separated by gel electrophoresis and the correct fragments were isolated. The three fragments were mixed with an EcoRV digested STABY vector with T4 ligase and ligation buffer. After overnight incubation at 16 C the complete mixtures were transformed to CYS21 competent cells (Eurogentec) and plated on 2xYT+100 µg/ml ampicillin and 2xYT+100 µg/ml ampicillin+20 µg/ml zeocin (50:50 v/v).

TABLE 4

STABY reaction

| Reaction | Insert | Cfu's on 2xYT | |
|---|---|---|---|
| | | +Amp | +Amp + Zeo |
| 1 | - (water) | 3 | 0 |
| 2 | niaDL-NcoI | 5 | 0 |
| 3 | NcoI-3310ble-SalI | 4 | 0 |
| 4 | SalI-niaDR*** | 6 | 0 |
| 5 | niaDL-NcoI + NcoI-3310ble-SalI + SalI-niaDR*** | 7 | 5 |

***= 14 bp ccdA complementation fragment

As can be extracted from table 4, STABY reactions also tend to produce false positive clones (see reactions 1-4 after plating out on 2xYT+ampicillin), which will disturb the actual triple fragment reaction (reaction 5). Here, the added value of the zeocin selection is clearly reducing the number of clones; i.e. discarding the false positives. Selected ampicillin and zeocin double positive clones were analysed via restriction enzyme analysis and shown to be correct.

SEQUENCE LISTING

<160> NUMBER OF SEQ ID NOS: 123

<210> SEQ ID NO 1
<211> LENGTH: 65
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)

<223> OTHER INFORMATION: n is a, c, g, or t
<220> FEATURE:
<221> NAME/KEY: misc_feature
<222> LOCATION: (31)..(51)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t

<400> SEQUENCE: 1
ttgacwnnnn nnnnnnnnnn nnyayaathh nnnnnnnnnn nnnnnnnnnn nsswkknnhm    60 mhatg    65

<210> SEQ ID NO 2
<211> LENGTH: 66
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(52)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 2
ttgacwnnnn nnnnnnnnnn nnnyayaath hnnnnnnnnn nnnnnnnnnn nnsswkknnh    60 mmhatg    66

<210> SEQ ID NO 3
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(53)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 3
ttgacwnnnn nnnnnnnnnn nnnnyayaat hhnnnnnnnn nnnnnnnnnn nnnsswkknn    60 hmmhatg    67

<210> SEQ ID NO 4
<211> LENGTH: 66
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(52)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 4
ttgacwnnnn nnnnnnnnnn nnyayaathh nnnnnnnnnn nnnnnnnnnn nnsswkknnh    60 mmhatg    66

<210> SEQ ID NO 5
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 5
ttgacwnnnn nnnnnnnnnn nnnyayaath hnnnnnnnnn nnnnnnnnnn nnnsswkknn    60 hmmhatg    67

<210> SEQ ID NO 6
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(54)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

<400> SEQUENCE: 6
ttgacwnnnn nnnnnnnnnn nnnnyayaat hhnnnnnnnn nnnnnnnnnn nnnnsswkkn    60 nhmmhatg    68

<210> SEQ ID NO 7
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:

<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 7
ttgacwnnnn nnnnnnnnnn nnyayaathh nnnnnnnnnn nnnnnnnnnn nnnsswkknn    60 hmmhatg                                                              67

<210> SEQ ID NO 8
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(54)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

<400> SEQUENCE: 8
ttgacwnnnn nnnnnnnnnn nnnyayaath hnnnnnnnnn nnnnnnnnnn nnnsswkkn     60 nhmmhatg                                                             68

<210> SEQ ID NO 9
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(55)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 9
ttgacwnnnn nnnnnnnnnn nnnnyayaat hhnnnnnnnn nnnnnnnnnn nnnnnsswkk    60 nnhmmhatg                                                            69

<210> SEQ ID NO 10
<211> LENGTH: 66
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature

```
<222> LOCATION: (31)..(51)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t

<400> SEQUENCE: 10
ttgacwnnnn nnnnnnnnnn nnyayaathh nnnnnnnnnn nnnnnnnnnn nsswkknnnh      60 mmhatg                                                                 66

<210> SEQ ID NO 11
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(52)
<223> OTHER INFORMATION: n is a, c, g, or t
<220> FEATURE:
<221> NAME/KEY: misc_feature
<222> LOCATION: (58)..(60)
<223> OTHER INFORMATION: n is a, c, g, or t

<400> SEQUENCE: 11
ttgacwnnnn nnnnnnnnnn nnnyayaath hnnnnnnnnn nnnnnnnnnn nnsswkknnn      60 hmmhatg                                                                67

<210> SEQ ID NO 12
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(53)
<223> OTHER INFORMATION: n is a, c, g, or t
<220> FEATURE:
<221> NAME/KEY: misc_feature
<222> LOCATION: (59)..(61)
<223> OTHER INFORMATION: n is a, c, g, or t

<400> SEQUENCE: 12
ttgacwnnnn nnnnnnnnnn nnnnyayaat hhnnnnnnnn nnnnnnnnnn nnnsswkknn      60 nhmmhatg                                                               68

<210> SEQ ID NO 13
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(52)
```

<223> OTHER INFORMATION: n is a, c, g, or t
<220> FEATURE:
<221> NAME/KEY: misc_feature
<222> LOCATION: (58)..(60)
<223> OTHER INFORMATION: n is a, c, g, or t

<400> SEQUENCE: 13
ttgacwnnnn nnnnnnnnnn nnyayaathh nnnnnnnnnn nnnnnnnnnn nnsswkknnn    60 hmmhatg                                                               67

<210> SEQ ID NO 14
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t
<220> FEATURE:
<221> NAME/KEY: misc_feature
<222> LOCATION: (59)..(61)
<223> OTHER INFORMATION: n is a, c, g, or t

<400> SEQUENCE: 14
ttgacwnnnn nnnnnnnnnn nnnyayaath hnnnnnnnnn nnnnnnnnnn nnnsswkknn    60 nhmmhatg                                                              68

<210> SEQ ID NO 15
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(54)
<223> OTHER INFORMATION: n is a, c, g, or t
<220> FEATURE:
<221> NAME/KEY: misc_feature
<222> LOCATION: (60)..(62)
<223> OTHER INFORMATION: n is a, c, g, or t

<400> SEQUENCE: 15
ttgacwnnnn nnnnnnnnnn nnnnyayaat hhnnnnnnnn nnnnnnnnnn nnnnsswkkn    60 nnhmmhatg                                                             69

<210> SEQ ID NO 16
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (59)..(61)
<223> OTHER INFORMATION: n is a, c, g, or t

<400> SEQUENCE: 16
ttgacwnnnn nnnnnnnnnn nnyayaathh nnnnnnnnnn nnnnnnnnnn nnnsswkknn    60 nhmmhatg                                                              68

<210> SEQ ID NO 17
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(54)
<223> OTHER INFORMATION: n is a, c, g, or t
<220> FEATURE:
<221> NAME/KEY: misc_feature
<222> LOCATION: (60)..(62)
<223> OTHER INFORMATION: n is a, c, g, or t

<400> SEQUENCE: 17
ttgacwnnnn nnnnnnnnnn nnnyayaath hnnnnnnnnn nnnnnnnnnn nnnnsswkkn    60 nnhmmhatg                                                             69

<210> SEQ ID NO 18
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(55)
<223> OTHER INFORMATION: n is a, c, g, or t
<220> FEATURE:
<221> NAME/KEY: misc_feature
<222> LOCATION: (61)..(63)
<223> OTHER INFORMATION: n is a, c, g, or t

<400> SEQUENCE: 18
ttgacwnnnn nnnnnnnnnn nnnnyayaat hhnnnnnnnn nnnnnnnnnn nnnnnsswkk    60 nnnhmmhatg                                                            70

<210> SEQ ID NO 19
<211> LENGTH: 67
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(51)
<223> OTHER INFORMATION: n is a, c, g, or t
<220> FEATURE:

```
<221> NAME/KEY: misc_feature
<222> LOCATION: (57)..(60)
<223> OTHER INFORMATION: n is a, c, g, or t

<400> SEQUENCE: 19
ttgacwnnnn nnnnnnnnnn nnyayaathh nnnnnnnnnn nnnnnnnnnn nsswkknnnn        60 hmmhatg                                                                  67

<210> SEQ ID NO 20
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(52)
<223> OTHER INFORMATION: n is a, c, g, or t
<220> FEATURE:
<221> NAME/KEY: misc_feature
<222> LOCATION: (58)..(61)
<223> OTHER INFORMATION: n is a, c, g, or t

<400> SEQUENCE: 20
ttgacwnnnn nnnnnnnnnn nnnyayaath hnnnnnnnnn nnnnnnnnnn nnsswkknnn        60 nhmmhatg                                                                 68

<210> SEQ ID NO 21
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(53)
<223> OTHER INFORMATION: n is a, c, g, or t
<220> FEATURE:
<221> NAME/KEY: misc_feature
<222> LOCATION: (59)..(62)
<223> OTHER INFORMATION: n is a, c, g, or t

<400> SEQUENCE: 21
ttgacwnnnn nnnnnnnnnn nnnnyayaat hhnnnnnnnn nnnnnnnnnn nnnsswkknn        60 nnhmmhatg                                                                69

<210> SEQ ID NO 22
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(52)
<223> OTHER INFORMATION: n is a, c, g, or t
<220> FEATURE:
<221> NAME/KEY: misc_feature
```

```
<222> LOCATION: (58)..(61)
<223> OTHER INFORMATION: n is a, c, g, or t

<400> SEQUENCE: 22
ttgacwnnnn nnnnnnnnnn nnyayaathh nnnnnnnnnn nnnnnnnnnn nnsswkknnn      60 nhmmhatg                                                               68

<210> SEQ ID NO 23
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t
<220> FEATURE:
<221> NAME/KEY: misc_feature
<222> LOCATION: (59)..(62)
<223> OTHER INFORMATION: n is a, c, g, or t

<400> SEQUENCE: 23
ttgacwnnnn nnnnnnnnnn nnnyayaath hnnnnnnnnn nnnnnnnnnn nnnsswkknn      60 nnhmmhatg                                                              69

<210> SEQ ID NO 24
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(54)
<223> OTHER INFORMATION: n is a, c, g, or t
<220> FEATURE:
<221> NAME/KEY: misc_feature
<222> LOCATION: (60)..(63)
<223> OTHER INFORMATION: n is a, c, g, or t

<400> SEQUENCE: 24
ttgacwnnnn nnnnnnnnnn nnnnyayaat hhnnnnnnnn nnnnnnnnnn nnnnsswkkn      60 nnnhmmhatg                                                             70

<210> SEQ ID NO 25
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (59)..(62)
```

<223> OTHER INFORMATION: n is a, c, g, or t

<400> SEQUENCE: 25
ttgacwnnnn nnnnnnnnnn nnyayaathh nnnnnnnnnn nnnnnnnnnn nnnsswkknn    60 nnhmmhatg    69

<210> SEQ ID NO 26
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(54)
<223> OTHER INFORMATION: n is a, c, g, or t
<220> FEATURE:
<221> NAME/KEY: misc_feature
<222> LOCATION: (60)..(63)
<223> OTHER INFORMATION: n is a, c, g, or t

<400> SEQUENCE: 26
ttgacwnnnn nnnnnnnnnn nnnyayaath hnnnnnnnnn nnnnnnnnnn nnnnsswkkn    60 nnnhmmhatg    70

<210> SEQ ID NO 27
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(55)
<223> OTHER INFORMATION: n is a, c, g, or t
<220> FEATURE:
<221> NAME/KEY: misc_feature
<222> LOCATION: (61)..(64)
<223> OTHER INFORMATION: n is a, c, g, or t

<400> SEQUENCE: 27
ttgacwnnnn nnnnnnnnnn nnnnyayaat hnnnnnnnnn nnnnnnnnnn nnnnnsswkk    60
nnnnhmmhat g    71

<210> SEQ ID NO 28
<211> LENGTH: 68
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(51)
<223> OTHER INFORMATION: n is a, c, g, or t
<220> FEATURE:
<221> NAME/KEY: misc_feature
<222> LOCATION: (57)..(61)
<223> OTHER INFORMATION: n is a, c, g, or t -continued

<400> SEQUENCE: 28
ttgacwnnnn nnnnnnnnnn nnyayaathh nnnnnnnnnn nnnnnnnnnn nsswkknnnn    60 nhmmhatg                                                              68

<210> SEQ ID NO 29
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(52)
<223> OTHER INFORMATION: n is a, c, g, or t
<220> FEATURE:
<221> NAME/KEY: misc_feature
<222> LOCATION: (58)..(62)
<223> OTHER INFORMATION: n is a, c, g, or t

<400> SEQUENCE: 29
ttgacwnnnn nnnnnnnnnn nnnyayaath hnnnnnnnnn nnnnnnnnnn nnsswkknnn     60 nnhmmhatg                                                             69

<210> SEQ ID NO 30
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(53)
<223> OTHER INFORMATION: n is a, c, g, or t
<220> FEATURE:
<221> NAME/KEY: misc_feature
<222> LOCATION: (59)..(63)
<223> OTHER INFORMATION: n is a, c, g, or t

<400> SEQUENCE: 30
ttgacwnnnn nnnnnnnnnn nnnnyayaat hhnnnnnnnn nnnnnnnnnn nnnsswkknn     60 nnnhmmhatg                                                            70

<210> SEQ ID NO 31
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(52)
<223> OTHER INFORMATION: n is a, c, g, or t
<220> FEATURE:
<221> NAME/KEY: misc_feature
<222> LOCATION: (58)..(62)
<223> OTHER INFORMATION: n is a, c, g, or t

<400> SEQUENCE: 31
ttgacwnnnn nnnnnnnnnn nnyayaathh nnnnnnnnnn nnnnnnnnnn nnsswkknnn    60 nnhmmhatg    69

<210> SEQ ID NO 32
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t
<220> FEATURE:
<221> NAME/KEY: misc_feature
<222> LOCATION: (59)..(63)
<223> OTHER INFORMATION: n is a, c, g, or t

<400> SEQUENCE: 32
ttgacwnnnn nnnnnnnnnn nnnyayaath hnnnnnnnnn nnnnnnnnnn nnnsswkknn    60 nnnhmmhatg    70

<210> SEQ ID NO 33
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(54)
<223> OTHER INFORMATION: n is a, c, g, or t
<220> FEATURE:
<221> NAME/KEY: misc_feature
<222> LOCATION: (60)..(64)
<223> OTHER INFORMATION: n is a, c, g, or t

<400> SEQUENCE: 33
ttgacwnnnn nnnnnnnnnn nnnnyayaat hhnnnnnnnn nnnnnnnnnn nnnnsswkkn    60
nnnnhmmhat g    71

<210> SEQ ID NO 34
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (59)..(63)
<223> OTHER INFORMATION: n is a, c, g, or t

<400> SEQUENCE: 34
ttgacwnnnn nnnnnnnnnn nnyayaathh nnnnnnnnnn nnnnnnnnnn nnnsswkknn    60 nnnhmmhatg                                                           70

<210> SEQ ID NO 35
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(54)
<223> OTHER INFORMATION: n is a, c, g, or t
<220> FEATURE:
<221> NAME/KEY: misc_feature
<222> LOCATION: (60)..(64)
<223> OTHER INFORMATION: n is a, c, g, or t

<400> SEQUENCE: 35
ttgacwnnnn nnnnnnnnnn nnnyayaath hnnnnnnnnn nnnnnnnnnn nnnnsswkkn    60
nnnnhmmhat g                                                         71

<210> SEQ ID NO 36
<211> LENGTH: 72
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(55)
<223> OTHER INFORMATION: n is a, c, g, or t
<220> FEATURE:
<221> NAME/KEY: misc_feature
<222> LOCATION: (61)..(65)
<223> OTHER INFORMATION: n is a, c, g, or t

<400> SEQUENCE: 36
ttgacwnnnn nnnnnnnnnn nnnnyayaat hhnnnnnnnn nnnnnnnnnn nnnnnsswkk    60
nnnnnhmmha tg                                                        72

<210> SEQ ID NO 37
<211> LENGTH: 69
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(51)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t

<400> SEQUENCE: 37
ttgacwnnnn nnnnnnnnnn nnyayaathh nnnnnnnnnn nnnnnnnnnn nsswkknnnn    60 nnhmmhatg    69

<210> SEQ ID NO 38
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(52)
<223> OTHER INFORMATION: n is a, c, g, or t
<220> FEATURE:
<221> NAME/KEY: misc_feature
<222> LOCATION: (58)..(63)
<223> OTHER INFORMATION: n is a, c, g, or t

<400> SEQUENCE: 38
ttgacwnnnn nnnnnnnnnn nnnyayaath hnnnnnnnnn nnnnnnnnnn nnsswkknnn    60 nnnhmmhatg    70

<210> SEQ ID NO 39
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(53)
<223> OTHER INFORMATION: n is a, c, g, or t
<220> FEATURE:
<221> NAME/KEY: misc_feature
<222> LOCATION: (59)..(64)
<223> OTHER INFORMATION: n is a, c, g, or t

<400> SEQUENCE: 39
ttgacwnnnn nnnnnnnnnn nnnnyayaat hhnnnnnnnn nnnnnnnnnn nnnsswkknn    60
nnnnhmmhat g    71

<210> SEQ ID NO 40
<211> LENGTH: 70
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(52)
<223> OTHER INFORMATION: n is a, c, g, or t
<220> FEATURE:
<221> NAME/KEY: misc_feature
<222> LOCATION: (58)..(63)
<223> OTHER INFORMATION: n is a, c, g, or t

<400> SEQUENCE: 40
ttgacwnnnn nnnnnnnnnn nnyayaathh nnnnnnnnnn nnnnnnnnnn nnsswkknnn    60 nnnhmmhatg 70

<210> SEQ ID NO 41
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t
<220> FEATURE:
<221> NAME/KEY: misc_feature
<222> LOCATION: (59)..(64)
<223> OTHER INFORMATION: n is a, c, g, or t

<400> SEQUENCE: 41
ttgacwnnnn nnnnnnnnnn nnnyayaath hnnnnnnnnn nnnnnnnnnn nnnsswkknn     60
nnnnhmmhat g     71

<210> SEQ ID NO 42
<211> LENGTH: 72
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(54)
<223> OTHER INFORMATION: n is a, c, g, or t
<220> FEATURE:
<221> NAME/KEY: misc_feature
<222> LOCATION: (60)..(65)
<223> OTHER INFORMATION: n is a, c, g, or t

<400> SEQUENCE: 42
ttgacwnnnn nnnnnnnnnn nnnnyayaat hhnnnnnnnn nnnnnnnnnn nnnsswkkn     60 nnnnnhmmha tg     72

<210> SEQ ID NO 43
<211> LENGTH: 71
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(22)
<223> OTHER INFORMATION: n is a, c, g, or t
<220> FEATURE:
<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (59)..(64)
<223> OTHER INFORMATION: n is a, c, g, or t

<400> SEQUENCE: 43
ttgacwnnnn nnnnnnnnnn nnyayaathh nnnnnnnnnn nnnnnnnnnn nnnsswkknn     60
nnnnhmmhat g 71

<210> SEQ ID NO 44
<211> LENGTH: 72
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(23)
<223> OTHER INFORMATION: n is a, c, g, or t
<220> FEATURE:
<221> NAME/KEY: misc_feature
<222> LOCATION: (32)..(54)
<223> OTHER INFORMATION: n is a, c, g, or t
<220> FEATURE:
<221> NAME/KEY: misc_feature
<222> LOCATION: (60)..(65)
<223> OTHER INFORMATION: n is a, c, g, or t

<400> SEQUENCE: 44
ttgacwnnnn nnnnnnnnn nnnyayaath hnnnnnnnnn nnnnnnnnnn nnnnsswkkn    60
nnnnnhmmha tg    72

<210> SEQ ID NO 45
<211> LENGTH: 73
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (33)..(55)
<223> OTHER INFORMATION: n is a, c, g, or t
<220> FEATURE:
<221> NAME/KEY: misc_feature
<222> LOCATION: (61)..(66)
<223> OTHER INFORMATION: n is a, c, g, or t

<400> SEQUENCE: 45
ttgacwnnnn nnnnnnnnn nnnnyayaat hhnnnnnnnn nnnnnnnnnn nnnnnsswkk    60
nnnnnnhmmh atg    73

<210> SEQ ID NO 46
<211> LENGTH: 68
<212> TYPE: DNA
<213> ORGANISM: Artificial Sequence
<220> FEATURE:
<223> OTHER INFORMATION: Synthetic DNA

<400> SEQUENCE: 46
ttgacttcgt cgttgtccac gcctataatt caagttttca ccattatttt tctggaggag    60
accatatg    68

<210> SEQ ID NO 47
<211> LENGTH: 68
<212> TYPE: DNA
<213> ORGANISM: Artificial Sequence
<220> FEATURE:
<223> OTHER INFORMATION: Synthetic DNA

<400> SEQUENCE: 47
ttgactagcc ctctcttcgt tgttataatc gccttcaagt tttcaccatt attggaggag    60

<210> SEQ ID NO 48
<211> LENGTH: 69
<212> TYPE: DNA
<213> ORGANISM: Artificial Sequence
<220> FEATURE:
<223> OTHER INFORMATION: Synthetic DNA

<400> SEQUENCE: 48
ttgactttcc cacttcatcg cagcataatt tgactaacag ctaccccgct tgaggaggac    60
atccatatg                                                            69

<210> SEQ ID NO 49
<211> LENGTH: 68
<212> TYPE: DNA
<213> ORGANISM: Artificial Sequence
<220> FEATURE:
<223> OTHER INFORMATION: Synthetic DNA

<400> SEQUENCE: 49
ttgactgagc tttcccactt tgtcataatt tgactaacag ctaccccgct tgaggaggca    60
tccatatg                                                             68

<210> SEQ ID NO 50
<211> LENGTH: 67
<212> TYPE: DNA
<213> ORGANISM: Artificial Sequence
<220> FEATURE:
<223> OTHER INFORMATION: Synthetic DNA

<400> SEQUENCE: 50
ttgactcttt tttgcctcct tttacaatct acccctttta atctttgcga ctcgtttctt    60
ccatatg                                                              67

<210> SEQ ID NO 51
<211> LENGTH: 67
<212> TYPE: DNA
<213> ORGANISM: Artificial Sequence
<220> FEATURE:
<223> OTHER INFORMATION: Synthetic DNA

<400> SEQUENCE: 51
ttgactcttt tttgcctcct tttacaatct acccattta atctttgcga ctggaggctt     60
ccatatg                                                              67

<210> SEQ ID NO 52
<211> LENGTH: 916
<212> TYPE: DNA
<213> ORGANISM: Streptomyces griseus

<400> SEQUENCE: 52
ggggacaagt tgtacaaaa aagcaggcta tttaaataga tctcctcgtc ccaccggctg     60
tcgaagctcc gcgcctacag cgccatcgac ttcgaccggg cgaagtagga agcggccggc   120
gacaaaacgg ggaggggcgg gaaacggtgg tccgtttccc gccccctgccc gtaggccgtg  180 cgcgtcccgc cggtgcgcgg cgttcagccc gccgcgcta tgtgctcggc cgtcgtcgcg   240
gcggccgtga gcccatatgc caagttgacc agtgccgttc cggtgctcac cgcgcgcgac   300
gtcgccggag cggtcgagtt ctggaccgac cggctcgggt tctcccggga cttcgtggag   360

| | |
|---|---|
| gacgacttcg ccggtgtggt ccgggacgac gtgaccctgt tcatcagcgc ggtccaggac | 420 |
| caggtggtgc cggacaacac cctggcctgg gtgtgggtgc gcggcctgga cgagctgtac | 480 |
| gccgagtggt cggaggtcgt gtccacgaac ttccgggacg cctccgggcc ggccatgacc | 540 |
| gagatcggcg agcagccgtg ggggcggag ttcgccctgc gcacccggcc cggcaactgc | 600 |
| gtgcacttcg tggccgagga gcaggactaa atgcattcct gggcaacaac ggtgttagcg | 660 |
| gtctttctgt gtaaaaatat taccccggc gtgcacgttc tactctggtg actctcatcc | 720 |
| tacttcattt catattcttt cttcaccta ccctccgcat gtcaccaggg ggtgtttctt | 780 |
| ggctcaaatc tggcccaatg tcggtagagg acgagctgcg tgccgctttc tcctaatcga | 840 |
| tggtgataac ttcgtatagc atacattata cgaagttata tttaaatacc cagctttctt | 900 |
| gtacaaagtg gtcccc | 916 |

<210> SEQ ID NO 53
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 53
ggtcgccacc atggtatcga tgggcgagga gc                                32

<210> SEQ ID NO 54
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 54
ggctgattat gatctagagt cgacgccgct ttaggcgccc agctcgtcca tgcc          54

<210> SEQ ID NO 55
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 55
gccattggct ctgtcaaggc gccgactaca gtactctgca tatgttgcat cgggaaatcc    60
cacc                                                                64

<210> SEQ ID NO 56
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 56
ggggacattg gccttgggca tcgatatcat gttaactaga aaataatgg                50

<210> SEQ ID NO 57
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 57

```
gtctaatcaa caagaagcgg ccgcacatga aagggcccat cgatggtcga ccgggatcta    60
gaaatcccgg actctgac                                                  78
```

<210> SEQ ID NO 58
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 58

```
gggaagacag tgtaagcggc cgcaagggtt cgtaattttt gtaag                    45
```

<210> SEQ ID NO 59
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 59

```
cagagcaaca ctcgaattct cgaagactag taagtac                             37
```

<210> SEQ ID NO 60
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 60

```
gtacttacta gtcttcgaga attcgagtgt tgctctg                             37
```

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 61

```
caattgtgtt tatgctgaga caacc                                          25
```

<210> SEQ ID NO 62
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 62

```
caattgtcag gcacacagga agagag                                         26
```

<210> SEQ ID NO 63
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 63

```
gtgtccggcg agggcgag                                                  18
```

<210> SEQ ID NO 64

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 64
caggtagtgg ttgtcggg                                                       18

<210> SEQ ID NO 65
<211> LENGTH: 774
<212> TYPE: DNA
<213> ORGANISM: Penicillium chrysogenum

<400> SEQUENCE: 65
atcgccgact acagtactct gcatatgttg catcgggaaa tcccaccaca gggacagcca         60
agcggccccg cgacttggca gtgggcaaac tacgcccgat tctggtgcca agaaccgaga        120
agaatgagac agaccacgt  tgcactctaa ccggatgcta tcgacttacg gtggctgaag        180
attcaacacg ctgcaacgag agccaaggtg gtccggacat tttctacgtg ccggtttacc        240
ttggaacatc gccgtcgttg agtgcacgtt gcctactctc tcgtggcttg gctgggccca        300
cgagcccgat tgactcgacg gtgttacttg ggtatctatg gccccgtttt ctggcacggt        360
aatgataagt acttactagt cttcgagcgg gggagtgttg ctctgcccga gcatcaacga        420
ttggcctgat cgcaccgtct gcaaatgcca cggtgcggac cgactgaaat ctcagaccac        480
caaagaccct ccgacttcga gatacggtta ctaattttac actggctcca gcggccccat        540
ccagtaagca tctgggctgc aagcgtataa tgtctccagg ttgtctcagc ataaacaccc        600
cgcccccgct caggcacaca ggaagagagc tcaggtcgtt tccattgcgt ccatactctt        660
cactcattgt catctgcagg agaacttccc ctgtcccttt gccaagccct ctcttcgtcg        720
ttgtccacgc cttcaagttt tcaccattat ttttctagtt aacatgatat cgat             774

<210> SEQ ID NO 66
<211> LENGTH: 774
<212> TYPE: DNA
<213> ORGANISM: Penicillium chrysogenum

<400> SEQUENCE: 66
atcgccgact acagtactct gcatatgttg catcgggaaa tcccaccaca gggacagcca         60
agcggccccg cgacttggca gtgggcaaac tacgcccgat tctggtgcca agaaccgaga        120
agaatgagac agaccacgt  tgcactctaa ccggatgcta tcgacttacg gtggctgaag        180
attcaacacg ctgcaacgag agccaaggtg gtccggacat tttctacgtg ccggtttacc        240
ttggaacatc gccgtcgttg agtgcacgtt gcctactctc tcgtggcttg gctgggccca        300
cgagcccgat tgactcgacg gtgttacttg ggtatctatg gccccgtttt ctggcacggt        360
aatgataagt acttactagt cttcgagaat tcgagtgttg ctctgcccga gcatcaacga        420
ttggcctgat cgcaccgtct gcaaatgcca cggtgcggac cgactgaaat ctcagaccac        480
caaagaccct ccgacttcga gatacggtta ctaattttac actggctcca gcggccccat        540
ccagtaagca tctgggctgc aagcgtataa tgtctccagg ttgtctcagc ataaacaccc        600
cgcccccgct caggcacaca ggaagagagc tcaggtcgtt tccattgcgt ccatactctt        660
cactcattgt catctgcagg agaacttccc ctgtcccttt gccaagccct ctcttcgtcg        720
ttgtccacgc cttcaagttt tcaccattat ttttctagtt aacatgatat cgat             774
```

```
<210> SEQ ID NO 67
<211> LENGTH: 768
<212> TYPE: DNA
<213> ORGANISM: Penicillium chrysogenum

<400> SEQUENCE: 67
atcgccgact acagtactct gcatatgttg catcgggaaa tcccaccaca gggacagcca        60
agcggccccg cgacttggca gtgggcaaac tacgcccgat tctggtgcca agaaccgaga       120
agaatgagac agaccacgt tgcactctaa ccggatgcta tcgacttacg gtggctgaag        180
attcaacacg ctgcaacgag agccaaggtg gtccggacat tttctacgtg ccggtttacc      240
ttggaacatc gccgtcgttg agtgcacgtt gcctactctc tcgtggcttg gctgggccca      300
cgagcccgat tgactcgacg gtgttacttg ggtatctatg gccccgtttt ctggcacggt      360
aatgataagt acttactagt cttcgagaat tcgagtgttg ctctgcccga gcatcaacga      420
ttggcctgat cgcaccgtct gcaaatgcca cggtgcggac cgactgaaat ctcagaccac      480
caaagaccct ccgacttcga gatacggtta ctaattttac actggctcca gcggccccat      540
ccagtaagca tctgggctgc aagcgtataa tgtctccagg ttgtctcagc ataaacacaa      600
ttgtcaggca cacaggaaga gagctcaggt cgtttccatt gcgtccatac tcttcactca      660
ttgtcatctg caggagaact tcccctgtcc ctttgccaag ccctctcttc gtcgttgtcc      720
acgccttcaa gttttcacca ttatttttct agttaacatg atatcgat                    768

<210> SEQ ID NO 68
<211> LENGTH: 1684
<212> TYPE: DNA
<213> ORGANISM: Artificial Sequence
<220> FEATURE:
<223> OTHER INFORMATION: Synthetic DNA

<400> SEQUENCE: 68
ggggacaagt ttgtacaaaa aagcaggcta tttaaatata acttcgtata gcatacatta        60
tacgaagtta ttcgactaca tgtatctgca tgttgcatcg ggaaatccca ccacagggac       120
agccaagcgg ccccgcgact tggcagtggg caaactacgc cgattctggt gccaagaac       180 cgagaagaat gagacagacc acgttgcac tctaaccgga tgctatcgac ttacggtggc      240
tgaagattca acacgctgca acgagagcca aggtggtccg acattttct acgtgccggt      300 ttaccttgga acatcgccgt cgttgagtgc acgttgccta ctctctcgtg gcttggctgg      360
acccacgagc ccgattgact cgacggtgtt acttgggtat ctatggcccc gttttctggc      420
acggtaatga taagtactta ctagtcttcg agaattcagt gttgctctgc ccgagcatca      480
acgattggcc tgatcgcacc gtctgcaaat gccacggtgc ggaccgactg aaatctcaga      540
ccaccaaaga ccctccgact tcgagatacg gttactaatt ttacactggc tccagcggcc      600
ccatccagta agcatctggg ctgcaagcgt ataatgtctc caggttgtct cagcataaac      660
acaattgtca ggcacacagg aagagagctc aggtcgtttc cattgcgtcc atactcttca      720
ctcattgtca tctgcaggag aacttcccct gtccctttgc caagccctct cttcgtcgtt      780
gtccacgcct tcaagttttc accattattt ttctagacca tatggccaag ttgaccagtg      840
ccgttccggt gctcaccgcg cgcgacgtcg ccggagcggt cgagtctgg accgaccggc      900 tcgggttctc ccgggacttc gtggaggacg acttcgccgg tgtggtccgg gacgacgtga      960
ccctgttcat cagcgcggtc caggaccagg tggtgccgga caacccctg gcctgggtgt     1020 gggtgcgcgg cctggacgag ctgtacgccg agtggtcgga ggtcgtgtcc acgaacttcc     1080
```

| | |
|---|---:|
| gggacgcctc cgggccggcc atgaccgaga tcggcgagca gccgtggggg cgggagttcg | 1140 |
| ccctgcgcga cccggccggc aactgcgtgc acttcgtggc cgaggagcag gactgatgca | 1200 |
| tgggaccggg atggaaatcc cggactctga gctaaaccga gtcgagaaaa aaagggagg | 1260 |
| agccgccacc atgccgccac cttcgtctac ctaattatcc atagccgaag ggtagataga | 1320 |
| cctagtcgtc gaatagttat tattttcacc atccatgcca aaatggttaa cgtgcatcgt | 1380 |
| tcctatgtga ccacgtagac catgccagtg attccatggc tgcctggccc ggtccagtag | 1440 |
| aagactgaac ctcttcgaga taacaagatt tttcttattg ttgtagcacg atgggtgggg | 1500 |
| tcacctcgtt ttcttcagct ctggctcctg aagatttgcg tggtagtgag ctgttttagg | 1560 |
| aaccacctgc attgaactaa attagtacga atcagcagaa ggaccacaga tctataactt | 1620 |
| cgtatagcat acattatacg aagttatatt taaatacccca gctttcttgt acaaagtggt | 1680 |
| cccc | 1684 |

<210> SEQ ID NO 69
<211> LENGTH: 1906
<212> TYPE: DNA
<213> ORGANISM: Artificial Sequence
<220> FEATURE:
<223> OTHER INFORMATION: Synthetic DNA

<400> SEQUENCE: 69

| | |
|---|---:|
| ggggacaagt ttgtacaaaa aagcaggcta tttaaatgaa ttccttatac tgggcctgct | 60 |
| gcattggtct gccattgcag ggtatatatg gctgacctgg ccaatctcca tcgagaatct | 120 |
| gggcgactga agaactgccc gcagacaaga tggagacttt cgtctagcac ggtctagggc | 180 |
| agatccgatg ccattggctc tgtcaactgt cgactacatg tatctgcatg ttgcatcggg | 240 |
| aaatcccacc acagggacag ccaagcggcc ccgcgacttg gcagtgggca aactacgccc | 300 |
| gattctggtg ccaagaaccg agaagaatga gacagaccca cgttgcactc taaccggatg | 360 |
| ctatcgactt acggtggctg aagattcaac acgctgcaac gagagccaag gtggtccgga | 420 |
| cattttctac gtgccggttt accttggaac atcgccgtcg ttgagtgcac gttgcctact | 480 |
| ctctcgtggc ttggctgggc ccacgagccc gattgactcg acggtgttac ttgggtatct | 540 |
| atggccccgt tttctggcac ggtaatgata agtacttact agtcttcgag aattcagtgt | 600 |
| tgctctgccc gagcatcaac gattggcctg atcgcaccgt ctgcaaatgc acggtgcgg | 660 |
| accgactgaa atctcagacc accaaagacc ctccgacttc gagatacggt tactaatttt | 720 |
| acactggctc cagcggcccc atccagtaag catctgggct gcaagcgtat aatgtctcca | 780 |
| ggttgtctca gcataaacac aattgtcagg cacacaggaa gagagctcag gtcgtttcca | 840 |
| ttgcgtccat actcttcact cattgtcatc tgcaggagaa cttcccctgt ccctttgcca | 900 |
| agccctctct tcgtcgttgt ccacgccttc aagttttcac cattattttt ctagaccata | 960 |
| aaaatttac aaaaggtat tgactttccc tacagggtgt gtaataattt aattacagct | 1020 |
| cgagaattaa aggagggttt catatggcca agttgaccag tgccgttccg gtgctcaccg | 1080 |
| cgcgcgacgt cgccggagcg gtcgagttct ggaccgaccg gctcgggttc tcccgggact | 1140 |
| tcgtggagga cgacttcgcc ggtgtggtcc gggacgacgt gaccctgttc atcagcgcgg | 1200 |
| tccaggacca ggtggtgccg acaacaccc tggcctgggt gtgggtgcgc ggcctggacg | 1260 |
| agctgtacgc cgagtggtcg gaggtcgtgt ccacgaactt ccggacgcc tccgggccgg | 1320 |
| ccatgaccga gatcggcgag cagcgtgggg gcgggagtt cgccctgcgc gacccggccg | 1380 |
| gcaactgcgt gcacttcgtg gccgaggagc aggactgatg catgggaccg ggatggaaat | 1440 |

```
cccggactct gagctaaacc gagtcgagaa aaaaaaggga ggagccgcca ccatgccgcc    1500
accttcgtct acctaattat ccatagccga agggtagata gacctagtcg tcgaatagtt    1560
attattttca ccatccatgc caaaatggtt aacgtgcatc gttcctatgt gaccacgtag    1620
accatgccag tgattccatg gctgcctggc ccggtccagt agaagactga acctcttcga    1680
gataacaaga ttttcttat tgttgtagca cgatgggtgg ggtcacctcg ttttcttcag     1740
ctctggctcc tgaagatttg cgtggtagtg agctgtttta ggaaccacct gcattgaact    1800
aaattagtac gaatcagcag aaggaccaca gatctataac ttcgtatagc atacattata    1860
cgaagttata tttaaatacc cagctttctt gtacaaagtg gtcccc                   1906
```

<210> SEQ ID NO 70
<211> LENGTH: 1818
<212> TYPE: DNA
<213> ORGANISM: Artificial Sequence
<220> FEATURE:
<223> OTHER INFORMATION: Synthetic DNA

<400> SEQUENCE: 70

```
ggggacaagt ttgtacaaaa aagcaggcta tttaaatata acttcgtata gcatacatta     60
tacgaagtta tgctctgtac agtgaccggt gactctttct ggcatgcgga gagacggacg    120
gacgcagaga gaagggctga gtaataagcc actggccaga cagctctggc ggctctgagg    180
tgcagtggat gattattaat ccgggaccgg ccgcccctcc gccccgaagt ggaaaggctg    240
gtgtgcccct cgttgaccaa gaatctattg catcatcgga gaatatggag cttcatcgaa    300
tcaccggcag taagcgaagg agaatgtgaa gccagggdtg tatagccgtc ggcgaaatag    360
catgccatta acctaggtac agaagtccaa ttgcttccga tctggtaaaa gattcacgag    420
atagtacctt ctccgaagta ggtagagcga gtacccggcg cgtaagctcc ctaattggcc    480
catccggcat ctgtagggcg tccaaatatc gtgcctctcc tgctttgccc ggtgtatgaa    540
accggaaagg ccgctcagga gctggccagc ggcgcagacc gggaacacaa gctggcagtc    600
gacccatccg gtgctctgca ctcgacctgc tgaggtccct cagtccctgg taggcagctt    660
tgccccgtct gtccgcccgg tgtgtcggcg gggttgacaa ggtcgttgcg tcagtccaac    720
atttgttgcc atattttcct gctctccca ccagctgctc ttttctttc tctttctttt     780 cccatcttca gtatattcat cttcccatcc aagaaccttt atttcccta agtaagtact      840 ttgctacatc catactccat ccttcccatc ccttattcct ttgaacccttt cagttcgagc    900 tttcccactt catcgcagct tgactaacag ctaccccgct tgagcagaca tccatatggc    960
caagttgacc agtgccgttc cggtgctcac cgcgcgcgac gtcgccggag cggtcgagtt   1020
ctggaccgac cggctcgggt tctccgggga cttcgtggag gacgacttcg ccggtgtggt   1080
ccgggacgac gtgaccctgt tcatcagcgc ggtccaggac caggtggtgc cggacaacac   1140
cctggcctgg gtgtgggtgc gcggcctgga cgagctgtac gccgagtggt cggaggtcgt   1200
gtccacgaac ttccgggacg cctccgggcc ggccatgacc gagatcggcg agcagccgtg   1260
ggggcgggag ttcgccctgc gcgacccggc cggcaactgc gtgcacttcg tggccgagga   1320
gcaggactga tgcatgggac cgggatggaa atcccggact ctgagctaaa ccgagtcgag   1380
aaaaaaaagg gaggagccgc caccatgccg ccaccttcgt ctacctaatt atccatagcc   1440
gaagggtaga tagacctagt cgtcgaatag ttattatttt caccatccat gccaaaatgg   1500
ttaacgtgca tcgttcctat gtgaccacgt agaccatgcc agtgattcca tggctgcctg   1560
```

| gcccggtcca gtagaagact gaacctcttc gagataacaa gattttttctt attgttgtag | 1620 |
| cacgatgggt ggggtcacct cgttttcttc agctctggct cctgaagatt tgcgtggtag | 1680 |
| tgagctgttt taggaaccac ctgcattgaa ctaaattagt acgaatcagc agaaggacca | 1740 |
| cagatctata acttcgtata gcatacatta tacgaagtta tatttaaata cccagctttc | 1800 |
| ttgtacaaag tggtcccc | 1818 |

<210> SEQ ID NO 71
<211> LENGTH: 1876
<212> TYPE: DNA
<213> ORGANISM: Artificial Sequence
<220> FEATURE:
<223> OTHER INFORMATION: Synthetic DNA

<400> SEQUENCE: 71

| ggggacaagt ttgtacaaaa aagcaggcta tttaaatgaa ttcgagctct gtacagtgac | 60 |
| cggtgactct ttctggcatg cggagagacg gacggacgca gagagaaggg ctgagtaata | 120 |
| agccactggc cagacagctc tggcggctct gaggtgcagt ggatgattat taatccggga | 180 |
| ccggccgccc ctccgccccg aagtggaaag gctggtgtgc ccctcgttga ccaagaatct | 240 |
| attgcatcat cggagaatat ggagcttcat cgaatcaccg gcagtaagcg aaggagaatg | 300 |
| tgaagccagg ggtgtatagc cgtcggcgaa atagcatgcc attaacctag gtacagaagt | 360 |
| ccaattgctt ccgatctggt aaaagattca cgagatagta ccttctccga agtaggtaga | 420 |
| gcgagtaccc ggcgcgtaag ctccctaatt ggcccatccg gcatctgtag ggcgtccaaa | 480 |
| tatcgtgcct ctcctgcttt gcccggtgta tgaaaccgga aaggccgctc aggagctggc | 540 |
| cagcggcgca gaccgggaac acaagctggc agtcgaccca tccggtgctc tgcactcgac | 600 |
| ctgctgaggt ccctcagtcc ctggtaggca gctttgcccc gtctgtccgc cggtgtgtc | 660 |
| ggcggggttg acaaggtcgt tgcgtcagtc caacatttgt tgccatattt tcctgctctc | 720 |
| cccaccagct gctctttcct tttctctttc ttttcccatc ttcagtatat tcatcttccc | 780 |
| atccaagaac ctttatttcc cctaagtaag tactttgcta catccatact ccatccttcc | 840 |
| catcccttat tcctttgaac ctttcagttc gagctttccc acttcatcgc agcttgacta | 900 |
| acagctaccc cgcttgagca gacatcacca aaaatttac aaaaaggtat tgactttccc | 960 |
| tacagggtgt gtaataattt aattacagct cgagaattaa aggagggttt catatggcca | 1020 |
| agttgaccag tgccgttccg gtgctcaccg cgcgcgacgt cgccggagcg gtcgagttct | 1080 |
| ggaccgaccg gctcgggttc tcccgggact cgtgtaggaga cgacttcgcc ggtgtggtcc | 1140 |
| gggacgacgt gaccctgttc atcagcgcgg tccaggacca ggtggtgccg acaacaccc | 1200 |
| tggcctgggt gtgggtgcgc ggcctggacg agctgtacgc cgagtggtcg gaggtcgtgt | 1260 |
| ccacgaactt ccgggacgcc tccgggccgg ccatgaccga gatcggcgag cagccgtggg | 1320 |
| ggcgggagtt cgccctgcgc gacccggccg gcaactgcgt gcacttcgtg gccgaggagc | 1380 |
| aggactgatg catgggaccg ggatggaaat cccggactct gagctaaacc gagtcgagaa | 1440 |
| aaaaaaggga ggagccgcca ccatgccgcc accttcgtct acctaattat ccatagccga | 1500 |
| agggtagata gacctagtcg tcgaatagtt attattttca ccatccatgc caaaatggtt | 1560 |
| aacgtgcatc gttcctatgt gaccacgtag accatgccag tgattccatg gctgcctggc | 1620 |
| ccggtccagt agaagactga acctcttcga gataacaaga ttttttcttat tgttgtagca | 1680 |
| cgatgggtgg ggtcacctcg ttttcttcag ctctggctcc tgaagatttg cgtggtagtg | 1740 |
| agctgtttta ggaaccacct gcattgaact aaattagtac gaatcagcag aaggaccaca | 1800 |

```
gatctataac ttcgtatagc atacattata cgaagttata tttaaatacc cagctttctt   1860
gtacaaagtg gtcccc                                                   1876

<210> SEQ ID NO 72
<211> LENGTH: 1700
<212> TYPE: DNA
<213> ORGANISM: Artificial Sequence
<220> FEATURE:
<223> OTHER INFORMATION: Synthetic DNA

<400> SEQUENCE: 72
ggggacaagt ttgtacaaaa aagcaggcta tttaaatata acttcgtata gcatacatta     60
tacgaagtta ttcgactaca tgtatctgca tgttgcatcg ggaaatccca ccacagggac    120
agccaagcgg ccccgcgact ggcagtggga caaactacgc ccgattctgg tgccaagaac    180
cgagaagaat gagacagacc cacgttgcac tctaaccgga tgctatcgac ttacggtggc    240
tgaagattca acacgctgca acgagagcca aggtggtccg acattttct acgtgccggt     300 ttaccttgga acatcgccgt cgttgagtgc acgttgccta ctctctcgtg gcttggctgg    360
acccacgagc ccgattgact cgacggtgtt acttgggtat ctatggcccc gttttctggc    420
acggtaatga taagtactta ctagtcttcg agaattcagt gttgctctgc ccgagcatca    480
acgattggcc tgatcgcacc gtctgcaaat gccacggtgc ggaccgactg aaatctcaga    540
ccaccaaaga ccctccgact tcgagatacg gttactaatt ttacactggc tccagcggcc    600
ccatccagta agcatctggg ctgcaagcgt ataatctctc caggttgtct cagcataaac    660
acaattgtca ggcacacagg aagagagctc aggtcgtttc cattgcgtcc atactcttca    720
ctcattgtca tctgcagaaa acttcccctg tcccttgcc aaaaagcccct ctttgacttc    780 gtcgttgtcc acgcctataa ttcaagtttt caccattatt tttctggagg agaccatatg    840
gccaagttga ccagtgccgt tccggtgctc accgcgcgcg acgtcgccgg agcggtcgag    900
ttctggaccg accggctcgg gttctcccgg gacttcgtgg aggacgactt cgccggtgtg    960
gtccgggacg acgtgaccct gttcatcagc gcggtccagg accaggtggt gccggacaac   1020
accctggcct gggtgtgggt gcgcggcctg gacgagctgt acgccgagtg gtcggaggtc   1080
gtgtccacga acttccggga cgcctccggg ccggccatga ccgagatcgg cgagcagccg   1140
tgggggcggg agttcgccct gcgcgacccg gccggcaact gcgtgcactt cgtggccgag   1200
gagcaggact gatgcatggg accgggatgg aaatcccgga ctctgagcta aaccgagtcg   1260
agaaaaaaaa gggaggagcc gccaccatgc cgccaccttc gtctacctaa ttatccatag   1320
ccgaagggta gatagaccta gtcgtcgaat agttattatt ttcaccatcc atgccaaaat   1380
ggttaacgtg catcgttcct atgtgaccac gtagaccatg ccagtgattc catggctgcc   1440
tggcccggtc cagtagaaga ctgaacctct tcgagataac aagatttttc ttattgttgt   1500
agcacgatgg gtggggtcac ctcgttttct tcagctctgg ctcctgaaga tttgcgtggt   1560
agtgagctgt tttaggaacc acctgcattg aactaaatta gtacgaatca gcagaaggac   1620
cacagatcta taacttcgta tagcatacat tatacgaagt tatatttaaa tacccagctt   1680
tcttgtacaa agtggtcccc                                              1700

<210> SEQ ID NO 73
<211> LENGTH: 1684
<212> TYPE: DNA
<213> ORGANISM: Artificial Sequence
<220> FEATURE:
```

<223> OTHER INFORMATION: Synthetic DNA

<400> SEQUENCE: 73

| | |
|---|---|
| gggggacaagt tgtacaaaa aagcaggcta tttaaatata acttcgtata gcatacatta | 60 |
| tacgaagtta ttcgactaca tgtatctgca tgttgcatcg ggaaatccca ccacagggac | 120 |
| agccaagcgg ccccgcgact tggcagtggg caaactacgc ccgattctgg tgccaagaac | 180 |
| cgagaagaat gagacagacc cacgttgcac tctaaccgga tgctatcgac ttacggtggc | 240 |
| tgaagattca acacgctgca acgagagcca aggtggtccg acatttctct acgtgccggt | 300 |
| ttaccttgga acatcgccgt cgttgagtgc acgttgccta ctctctcgtg gcttggctgg | 360 |
| acccacgagc ccgattgact cgacggtgtt acttgggtat ctatggcccc gttttctggc | 420 |
| acggtaatga taagtactta ctagtcttcg agaattcagt gttgctctgc ccgagcatca | 480 |
| acgattggcc tgatcgcacc gtctgcaaat gccacggtgc ggaccgactg aaatctcaga | 540 |
| ccaccaaaga ccctccgact tcgagatacg gttactaatt ttacactggc tccagcggcc | 600 |
| ccatccagta agcatctggg ctgcaagcgt ataatgtctc caggttgtct cagcataaac | 660 |
| acaattgtca ggcacacagg aagagagctc aggtcgtttc cattgcgtcc atactcttca | 720 |
| ctcattgtca tctgcagaaa aacttcccct gtccctttga ctagccctct cttcgttgtt | 780 |
| ataatcgcct tcaagttttc accattattg gaggagacca tatggccaag ttgaccagtg | 840 |
| ccgttccggt gctcaccgcg cgcgacgtcg ccggagcggt cgagtctctgg accgaccggc | 900 |
| tcgggttctc ccgggacttc gtggaggacg acttcgccgg tgtggtccgg gacgacgtga | 960 |
| ccctgttcat cagcgcggtc caggaccagg tggtgccgga caacaccctg gcctgggtgt | 1020 |
| gggtgcgcgg cctggacgag ctgtacgccg agtggtcgga ggtcgtgtcc acgaacttcc | 1080 |
| gggacgcctc cggccggcc atgaccgaga tcggcgagca gccgtggggg cgggagttcg | 1140 |
| ccctgcgcga cccggccggc aactgcgtgc acttcgtggc cgaggagcag gactgatgca | 1200 |
| tgggaccggg atggaaatcc cggactctga gctaaaccga gtcgagaaaa aaagggagg | 1260 |
| agccgccacc atgccgccac cttcgtctac ctaattatcc atagccgaag ggtagataga | 1320 |
| cctagtcgtc gaatagttat tatttttcacc atccatgcca aaatggttaa cgtgcatcgt | 1380 |
| tcctatgtga ccacgtagac catgccagtg attccatggc tgcctggccc ggtccagtag | 1440 |
| aagactgaac ctcttcgaga taacaagatt tttcttattg ttgtagcacg atgggtgggg | 1500 |
| tcacctcgtt ttcttcagct ctggctcctg aagatttgcg tggtagtgag ctgttttagg | 1560 |
| aaccacctgc attgaactaa attagtacga atcagcagaa ggaccacaga tctataactt | 1620 |
| cgtatagcat acattatacg aagttatatt taaatacca gctttcttgt acaaagtggt | 1680 |
| cccc | 1684 |

<210> SEQ ID NO 74
<211> LENGTH: 1835
<212> TYPE: DNA
<213> ORGANISM: Artificial Sequence
<220> FEATURE:
<223> OTHER INFORMATION: Synthetic DNA

<400> SEQUENCE: 74

| | |
|---|---|
| gggggacaagt tgtacaaaa aagcaggcta tttaaatata acttcgtata gcatacatta | 60 |
| tacgaagtta tgctctgtac agtgaccggt gactctttct ggcatgcgga gagacggacg | 120 |
| gacgcagaga gaagggctga gtaataagcc actggccaga cagctctggc ggctctgagg | 180 |
| tgcagtggat gattattaat ccgggaccgg ccgcccctcc gccccgaagt ggaaaggctg | 240 |

```
gtgtgcccct cgttgaccaa gaatctattg catcatcgga gaatatggag cttcatcgaa      300
tcaccggcag taagcgaagg agaatgtgaa gccaggggtg tatagccgtc ggcgaaatag      360
catgccatta acctaggtac agaagtccaa ttgcttccga tctggtaaaa gattcacgag      420
atagtacctt ctccgaagta ggtagagcga gtacccggcg cgtaagctcc ctaattggcc      480
catccggcat ctgtagggcg tccaaatatc gtgcctctcc tgctttgccc ggtgtatgaa      540
accgaaaagg ccgctcagga gctggccagc ggcgcagacc gggaacacaa gctggcagtc      600
gacccatccg gtgctctgca ctcgacctgc tgaggtccct cagtccctgg taggcagctt      660
tgccccgtct gtccgcccgg tgtgtcggcg gggttgacaa ggtcgttgcg tcagtccaac      720
atttgttgcc atattttcct gctctcccca ccagctgctc ttttctttc tctttctttt       780 cccatcttca gtatattcat cttcccatcc aagaaccttt atttccccta agtaagtact      840
ttgctacatc catactccat ccttcccatc ccttattcct ttgaaaaacc tttcaaaaag      900
ttcgagttga ctttcccact tcatcgcagc ataatttgac taacagctac cccgcttgag      960
gaggacatcc atatggccaa gttgaccagt gccgttccgg tgctcaccgc gcgcgacgtc     1020 gccgagcgt cgagttctg daccgaccgg ctcgggttct cccggacttc gtggaggac       1080 gacttcgccg gtgtggtccg ggacgacgtg accctgttca tcagcgcggt ccaggaccag     1140
gtggtgccgg acaacaccct ggcctgggtg tgggtgcgcg gcctgaacga gctgtacgcc     1200
gagtggtcgg aggtcgtgtc cacgaacttc cgggacgcct ccgggccggc catgaccgag     1260
atcggcgagc agccgtgggg gcgggagttc gccctgcgcg accggccgg caactgcgtg     1320 cacttcgtgg ccgaggagca ggactgatgc atgggaccgg gatggaaatc ccggactctg     1380
agctaaaccg agtcgagaaa aaaagggag gagccgccac catgccgcca ccttcgtcta     1440
cctaattatc catagccgaa gggtagatag acctagtcgt cgaatagtta ttattttcac     1500
catccatgcc aaaatggtta acgtgcatcg ttcctatgtg accacgtaga ccatgccagt     1560
gattccatgg ctgcctggcc cggtccagta gaagactgaa cctcttcgag ataacaagat     1620
ttttcttatt gttgtagcac gatgggtggg gtcacctcgt tttcttcagc tctggctcct     1680
gaagatttgc gtggtagtga gctgttttag gaaccacctg cattgaacta aattagtacg     1740
aatcagcaga aggaccacag atctataact tcgtatagca tacattatac gaagttatat     1800
ttaaataccc agctttcttg tacaaagtgg tcccc                                1835
```

<210> SEQ ID NO 75
<211> LENGTH: 1821
<212> TYPE: DNA
<213> ORGANISM: Artificial Sequence
<220> FEATURE:
<223> OTHER INFORMATION: Synthetic DNA

<400> SEQUENCE: 75

```
ggggacaagt tgtacaaaaa aagcaggcta tttaaatata acttcgtata gcatacatta       60
tacgaagtta tgctctgtac agtgaccggt gactcttct ggcatgcgga gagacggacg      120
gacgcagaga gaagggctga gtaataagcc actggccaga cagctctggc ggctctgagg      180
tgcagtggat gattattaat ccgggaccgg ccgccctcc gccccgaagt ggaaaggctg       240
gtgtgcccct cgttgaccaa gaatctattg catcatcgga gaatatggag cttcatcgaa      300
tcaccggcag taagcgaagg agaatgtgaa gccaggggtg tatagccgtc ggcgaaatag      360
catgccatta acctaggtac agaagtccaa ttgcttccga tctggtaaaa gattcacgag      420
```

| | |
|---|---|
| atagtacctt ctccgaagta ggtagagcga gtacccggcg cgtaagctcc ctaattggcc | 480 |
| catccggcat ctgtagggcg tccaaatatc gtgcctctcc tgctttgccc ggtgtatgaa | 540 |
| accggaaagg ccgctcagga gctggccagc ggcgcagacc gggaacacaa gctggcagtc | 600 |
| gacccatccg gtgctctgca ctcgacctgc tgaggtccct cagtccctgg taggcagctt | 660 |
| tgccccgtct gtccgcccgg tgtgtcggcg gggttgacaa ggtcgttgcg tcagtccaac | 720 |
| atttgttgcc atattttcct gctctcccca ccagctgctc tttcttttc tctttctttt | 780 |
| cccatcttca gtatattcat cttcccatcc aagaaccttt atttccccta gtaagtact | 840 |
| ttgctacatc catactccat ccttcccatc ccttattcct ttgaaaaacc tttttgactg | 900 |
| agctttccca ctttgtcata atttgactaa cagctacccc gcttgaggag gcatccatat | 960 |
| ggccaagttg accagtgccg ttccggtgct caccgcgcgc gacgtcgccg gagcggtcga | 1020 |
| gttctggacc gaccggctcg ggttctcccg ggacttcgtg gaggacgact cgccggtgt | 1080 |
| ggtccgggac gacgtgaccc tgttcatcag cgcggtccag gaccaggtgg tgccggacaa | 1140 |
| caccctggcc tgggtgtggg tgcgcggcct ggacgagctg tacgccgagt ggtcggaggt | 1200 |
| cgtgtccacg aacttccggg acgcctccgg gccggccatg accgagatcg gcgagcagcc | 1260 |
| gtgggggcgg gagttcgccc tgcgcgaccc ggccggcaac tgcgtgcact tcgtggccga | 1320 |
| ggagcaggac tgatgcatgg gacccggatg gaaatcccgg actctgagct aaaccgagtc | 1380 |
| gagaaaaaaa agggaggagc cgccaccatg ccgccacctt cgtctaccta attatccata | 1440 |
| gccgaagggt agatagacct agtcgtcgaa tagttattat tttcaccatc catgccaaaa | 1500 |
| tggttaacgt gcatcgttcc tatgtgacca cgtagaccat gccagtgatt ccatggctgc | 1560 |
| ctggcccggt ccagtagaag actgaacctc ttcgagataa caagattttt cttattgttg | 1620 |
| tagcacgatg ggtggggtca cctcgttttc ttcagctctg gctcctgaag atttgcgtgg | 1680 |
| tagtgagctg tttaggaac cacctgcatt gaactaaatt agtacgaatc agcagaagga | 1740 |
| ccacagatct ataacttcgt atagcataca ttatacgaag ttatatttaa atacccagct | 1800 |
| ttcttgtaca aagtggtccc c | 1821 |

```
<210> SEQ ID NO 76
<211> LENGTH: 1091
<212> TYPE: DNA
<213> ORGANISM: Penicillium chrysogenum

<400> SEQUENCE: 76
```

| | |
|---|---|
| ggggacaagt tgtacaaaa aagcaggcta tttaaatata acttcgtata gcatacatta | 60 |
| tacgaagtta ttcagccaca ggccggaagg tggtgtcccg cgaggaaaaa agagtgtggc | 120 |
| cactccccaa gccccccag aggacactaa agctcggtct agttgttcgg aggaaccccc | 180 |
| tgattggctc tccacttttg gattgtcaaa aagttgcttg ggattcgact ctcttattta | 240 |
| tttccccttt ctcctacttc tccaagtcgc tatccattcc cttcaattgt cttctcttgc | 300 |
| ttcgcttctc ttgtggtatt tccaatcttg gtttaccttg tctttttctc ttggaaagtc | 360 |
| ttggaaattg actctttttt gcctcctttt acaatctacc ccttttaatc tttgcgactc | 420 |
| gtttcttcca tatgccaagt tgaccagtgc cgttccggtg ctcaccgcgc gcgacgtcgc | 480 |
| cggagcggtc gagttctgga ccgaccggct cgggttctcc cgggacttcg tggaggacga | 540 |
| cttcgccggt gtggtccggg acgacgtgac cctgttcatc agcgcggtcc aggaccaggt | 600 |
| ggtgccggac aacaccctgg cctgggtgtg gtgcgcggc ctggacgagc tgtacgccga | 660 |
| gtggtcggag gtcgtgtcca cgaacttccg ggacgcctcc gggccggcca tgaccgagat | 720 |

```
cggcgagcag ccgtgggggc gggagttcgc cctgcgcgac ccggccggca actgcgtgca    780
cttcgtggcc gaggagcagg actaaatgca ttcctgggca acaacggtgt tagcggtctt    840
tctgtgtaaa aatattaccc ccggcgtgca cgttctactc tggtgactct catcctactt    900
catttcatat tctttcttca ccttaccctc cgcatgtcac caggggggtgt ttcttggctc    960 aaatctggcc caatgtcggt agaggacgag ctgcgtgccg ctttctccta atcgatggtg   1020
ataacttcgt atagcataca ttatacgaag ttatatttaa atacccagct ttcttgtaca   1080
aagtggtccc c                                                        1091
```

<210> SEQ ID NO 77
<211> LENGTH: 1091
<212> TYPE: DNA
<213> ORGANISM: Penicillium chrysogenum

<400> SEQUENCE: 77

```
ggggacaagt tgtacaaaaa aagcaggcta tttaaatata acttcgtata gcatacatta     60
tacgaagtta ttcagccaca ggccggaagg tggtgtcccg cgaggaaaaa agagtgtggc    120
cactccccaa gccccccccag aggacactaa agctcggtct agttgttcgg aggaaccccc   180
tgattggctc tccacttttg gattgtcaaa aagttgcttg ggattcgact ctcttattta    240
tttccccttt ctcctacttc tccaagtcgc tatccattcc cttcaattgt cttctcttgc    300
ttcgcttctc ttgtggtatt tccaatcttg gtttaccttg tcttttttctc ttggaaagtc   360 ttggaaattg actcttttttt gcctcctttt acaatctacc catttttaatc tttgcgactg   420 gaggcttcca tatgccaagt tgaccagtgc cgttccggtc ctcaccgcgc gcgacgtcgc    480
cggagcggtc gagttctgga ccgaccggct cgggttctcc cgggacttcg tgaggacga    540 cttcgccggt gtggtccggg acgacgtgac cctgttcatc agcgcggtcc aggaccaggt    600
ggtgccggac aacaccctgg cctgggtgtg ggtgcgcggc ctggacgagc tgtacgccga    660
gtggtcggag gtcgtgtcca cgaacttccg ggacgcctcc gggccggcca tgaccgagat    720
cggcgagcag ccgtgggggc gggagttcgc cctgcgcgac ccggccggca actgcgtgca    780
cttcgtggcc gaggagcagg actaaatgca ttcctgggca acaacggtgt tagcggtctt    840
tctgtgtaaa aatattaccc ccggcgtgca cgttctactc tggtgactct catcctactt    900
catttcatat tctttcttca ccttaccctc cgcatgtcac caggggggtgt ttcttggctc    960 aaatctggcc caatgtcggt agaggacgag ctgcgtgccg ctttctccta atcgatggtg   1020
ataacttcgt atagcataca ttatacgaag ttatatttaa atacccagct ttcttgtaca   1080
aagtggtccc c                                                        1091
```

<210> SEQ ID NO 78
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 78

```
catcctgact ataagctaac accatatgcc ttcgaactgg aagaactgg              50
```

<210> SEQ ID NO 79
<211> LENGTH: 47
<212> TYPE: DNA
<213> ORGANISM: Artificial Sequence
<220> FEATURE:

<223> OTHER INFORMATION: Synthetic oligonucleotide

<400> SEQUENCE: 79
ttgtgcaaat tgctatctga cacttatgca tgctatggag tcaccac         47

<210> SEQ ID NO 80
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 80
gaattcaacg tttacaattt cgcctgatgc ggtattttc         39

<210> SEQ ID NO 81
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 81
catatgggtg gccctcctca cgtgctttat tcaag         35

<210> SEQ ID NO 82
<211> LENGTH: 125
<212> TYPE: DNA
<213> ORGANISM: Artificial Sequence
<220> FEATURE:
<223> OTHER INFORMATION: Synthetic oligonucleotide

<400> SEQUENCE: 82
ttgaagacgt ggcccagact gtccgctgtg taaaaataag gaataaaggg gggttgttat         60
tattttactg atatgtaaaa tataatttgt ataagaaaat acaagtttgt acaaaaaagc         120
tgaac         125

<210> SEQ ID NO 83
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 83
aaggatctcg tcttcaccac tttgtacaag aaagctgaac         40

<210> SEQ ID NO 84
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(11)
<223> OTHER INFORMATION: n is a, c, g, or t

<400> SEQUENCE: 84
acccgggnnn nawaaas         17

<210> SEQ ID NO 85
<211> LENGTH: 16
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t

<400> SEQUENCE: 85
tatcgatdnc atkkkk                                                      16

<210> SEQ ID NO 86
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 86
catcctgact ataagctaac accatatgcc ttcgaactgg gaagaactgg                  50

<210> SEQ ID NO 87
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 87
ttgtgcaaat tgctatctga cacttatgca tgctatggag tcaccac                     47

<210> SEQ ID NO 88
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 88
caggaacagc tatgac                                                      16

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
cttgacgtag aagacggcac cggc                                             24

<210> SEQ ID NO 90
<211> LENGTH: 73
<212> TYPE: DNA
<213> ORGANISM: Penicillium chrysogenum

<400> SEQUENCE: 90
gaatctttct ctgcgccacg cgacctgccc gatttcgtcg acgcaacccg cgtcacctcc      60
gacatgaccc atg                                                         73

<210> SEQ ID NO 91
<211> LENGTH: 193
<212> TYPE: DNA
<213> ORGANISM: Penicillium chrysogenum

<400> SEQUENCE: 91
```

```
gaattcgccc ttacccggga gtcataaact aatttatacc tgtacgtttc tcataatatg    60
agtcctagag gaggactcag gacaagtccg gaccgccagg acccacatgg aggtcatgtt   120
tggcatagcg tagccgccgt gcattagcgt caaaactcta accaatcttg tactagtttg   180
ggtagataga atg                                                     193
```

<210> SEQ ID NO 92
<211> LENGTH: 460
<212> TYPE: DNA
<213> ORGANISM: Penicillium chrysogenum

<400> SEQUENCE: 92

```
gaattcgccc ttacccgggg tggataaacc acatagcaag ctatagaact aaataggtg    60 ttcatttaca aagttcgttc ataaatgagg gtttcatgcc aaacaaatct agcctcttat   120
gcttctaaat tcatggtagc tggaagtaaa atggcaggca gaatgggcca ttcatttacc   180
atgcacatgc tttgttgatt atccgtcaaa gcccttccaa tcttggaagc cctggagggt   240
ccacggcccc gggggttgat agtgattatg taaatccatg ctttatccaa cccgggtaag   300
ggcgaattcg cccttacccg gggtggataa accacaggcg ctgcgccgtt cagatacttc   360
aacacacacg cactcctcga gcgcgcaatt gccgtgtcaa gcccaacatt ctctccccga   420
ctcttatcct tcttatcctt tttctcgatc agaccccatg                        460
```

<210> SEQ ID NO 93
<211> LENGTH: 393
<212> TYPE: DNA
<213> ORGANISM: Penicillium chrysogenum

<400> SEQUENCE: 93

```
gaattcgctt ccacggcaag acaatcaagg actgccagaa ggaattgccc aagggcacga    60
ccggcacaga aatgctaccc gaggccatgt tctggctgtt gctgacgggc caggtgccct   120
ctacggggca ggttcgtgcc ttttcgcgcg aactggccga gaagtctgaa ctccccgccc   180
acattctgga cctgatcaag tctttccctg cctcaatgca tcctatgacc caactatcaa   240
ttgctgtagc agcgctcaat accgaatcca agttcgccaa ggcctacgag aacggcatca   300
acaaggccga ctactgggag ccaacctttg acgacagcat ctccctcctt gccaagatcc   360
ctcgcgtggc agcacttgtc ttccgtccca atg                               393
```

<210> SEQ ID NO 94
<211> LENGTH: 516
<212> TYPE: DNA
<213> ORGANISM: Penicillium chrysogenum

<400> SEQUENCE: 94

```
gaattcgccc ttacccgggc ggcaaaaagc aatgactact acctagaata tcacatgcga    60
aattcatgct tttccaccat agtccacgcc caatagccca gagagctcaa ccctgcgaga   120
atcgagatcg agaacaaccc cagccctgtc agaatgcctt gctcaaaaaa ccctacacct   180
ccacccaagg gccgccgagt ccggcaggcc agttgactcg actgcaagtc cagcatattc   240
tgcaaggctg atggtgattt ggcacgtaga atatccgtga cagactgcga cagcccggta   300
gggcggatat aatgtggccg aggaacggag aagaccgtag ttgggtatct cactgagcga   360
tccagggcca cttgtttagg ggcagggggt cccactagaa gggataaaat tatattagtg   420
ctgtaaacat catttaaacg aaaaagttta actgcgatcc ccttacccag gacttccaca   480
gggatgtggt tgacaaacga gacatgcgcg ttaatg                            516
```

<210> SEQ ID NO 95
<211> LENGTH: 189
<212> TYPE: DNA
<213> ORGANISM: Penicillium chrysogenum

<400> SEQUENCE: 95

| | | | | | |
|---|---|---|---|---|---|
| gaattcgccc | ttacccgggt | tgtataaaga | accttgaaat | gacgcaggta | ttagtgggat | 60 |
| caattcaaaa | tcccacaaaa | tcccacaaca | ttggggagaa | tagggagaa | taggagacag | 120 |
| atccagatat | cccaactggc | ggtgtctttc | tagcgtgggg | gtgagttacg | gtaataccga | 180 |
| atacccatg | | | | | | 189 |

<210> SEQ ID NO 96
<211> LENGTH: 462
<212> TYPE: DNA
<213> ORGANISM: Penicillium chrysogenum

<400> SEQUENCE: 96

| | | | | | |
|---|---|---|---|---|---|
| gaattcgccc | ttacccgggt | gggaaaaagc | aagggatatt | tgggcggtta | tataggttag | 60 |
| ccatcaaagc | cggccatgca | cagtctaaca | acgggaagtt | gccaaagaaa | gaagcataaa | 120 |
| gacattgttg | actctttagg | tctttgtcct | tcgttcttc | acacaaagac | ataaaagata | 180 |
| ctcaaagaaa | acgaggcatt | ccactttata | gacgaatttg | aaacaatgat | ggaacatagt | 240 |
| cagatttgca | gaaaagctat | gtacagcaga | aatagagaga | tcaccgaatg | gcagacgctc | 300 |
| taaacacctt | gcagaccctg | aaaaggcaaa | gaaaaatgac | gctgaagcaa | acataagat | 360 |
| gaaaatcaaa | gaaataaaaa | tggaaagtag | aaagtagaaa | gcaaaactca | agaaagcgca | 420 |
| gtattgtagg | ctttttcatt | cgcgcggaga | accaacccca | tg | | 462 |

<210> SEQ ID NO 97
<211> LENGTH: 677
<212> TYPE: DNA
<213> ORGANISM: Penicillium chrysogenum

<400> SEQUENCE: 97

| | | | | | |
|---|---|---|---|---|---|
| gaattccatg | agactgaaca | atgtgaagac | ggagtataat | acaagcaatg | gctacggaac | 60 |
| acggcactca | ttctaatttt | aagagaaata | aatgcctcat | tccactcggt | ctgatactac | 120 |
| gtctgtgaca | ctacgatgtg | agtcgtacga | atggaagcta | atcagagtat | gtcggaagaa | 180 |
| gcaggagtgc | atttcatcag | gagataactc | ggataagtcg | gttgggaagt | tggttggaat | 240 |
| ctccgcggag | atgagtggtt | ttatgtcggc | tgtgattggt | ccgattgggt | tgggttaggg | 300 |
| tttgcttatc | ttaacgtctg | gagataagaa | tgcagattac | ctacatggat | acttgggtac | 360 |
| atccatgggt | ccgattgcac | ttggaatgac | ttgactcggt | gatattctgg | gaatgtggag | 420 |
| aagagggcat | ggattccgcg | gagatctgaa | aactgctcat | gttgatggtg | atattggaat | 480 |
| ggggctgagg | gctgagggcc | tgggtacata | ctgctattcg | cagtcaattg | tgggtattt | 540 |
| ggacgtaaag | actgtctcga | tatattctac | tcagattta | ttgagttatt | tgtcttactt | 600 |
| caagaagcaa | tttcaacagt | tttcattata | taccaacggt | ttgatagcac | aaatcagcgt | 660 |
| aggatcgcgt | ccatatg | | | | | 677 |

<210> SEQ ID NO 98
<211> LENGTH: 270
<212> TYPE: DNA
<213> ORGANISM: Penicillium chrysogenum

```
<400> SEQUENCE: 98
gaattcgccc ttacccgggg gggataaact gtcggagcac ttacaggggc gaatataatc    60
cgtcatccag tcccttcgac gcagcatgac tgactcgacc tccggtggcg taaactaggt   120
aacccaggga ccgcaagaca ataaagaaga tgcccgtgtt ctccatgcag tacccatcta   180
gccgccgctc caccatcttc tcaaagagat tctgcgggtt cagagagata gtatgatgtt   240
gcgagtaatg cagccccgag ttgccccatg                                    270

<210> SEQ ID NO 99
<211> LENGTH: 338
<212> TYPE: DNA
<213> ORGANISM: Penicillium chrysogenum

<400> SEQUENCE: 99
gaattcgccc ttacccgggg tggaaaaagg caagtattag gtcccgctgc cgccgtagct    60
aaccacaacc ccatccagaa gaaaagaag gaggactccg cagcccgcga cacgcctgca    120
tccatacgga ttttcatcct acaatcaaga tggacgctgt gatgcggcag caggggttgg   180
acgatgtcag cgtctgtgtc tacacttaac caactccaca aggagcgcct acaatgctgt   240
cgacgtccga attggtacca atatatcgat cctttcatgc ccccgagccg agcagggatt   300
gaagaaatta gctacagcca ttctttttctt gcccaatg                          338

<210> SEQ ID NO 100
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 100
ggggacaact ttgtatagaa aagttggcgg ccgcggatcc gatcctcgat cttgcgatgt    60
ttc                                                                  63

<210> SEQ ID NO 101
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 101
ggggactgct tttttgtaca aacttgccgt agaatccatt cggctatgg                49

<210> SEQ ID NO 102
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 102
ggggacagct ttcttgtaca aagtgggagg tggccgaaga ataacaaaag                50

<210> SEQ ID NO 103
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 103
```

```
gggacaactt tgtataataa agttgggtac cgccagggaa ttcttgccac tccgtttatc    60
catactg                                                              67

<210> SEQ ID NO 104
<211> LENGTH: 2089
<212> TYPE: DNA
<213> ORGANISM: Artificial Sequence
<220> FEATURE:
<223> OTHER INFORMATION: Synthetic DNA

<400> SEQUENCE: 104
ggggacaact tgtatagaaa agttggcgg ccgcactggt tgctctgaat agaggcatgt    60
ggttctgtat agggttctga atagtgttct ttgtcgacat cagcctgaat aaaggtactg   120
ctcgagatcg gcagttctca ataggaatct tattgaccga cgtcagtgtg ccactccaat   180
aaggacctca ggtctcgtat agagagggtc tagggcaagc catcctgtcg aatgctttga   240
cggacaagtc ggctaataaa ccaagttaat tgagctggag tatattagtc aagatggtag   300
atatatttct ttggtcgatt tgaccacgat ctccggggta tgacatattc gaggacccga   360
agaggatatg aataagaatt gacgaaagaa atgtagtttc gaggggtaa atgaataag     420 aatgtaagtt tcattgtctc attgtttgga agttgaacgg aggcacctca agagaccctc   480
agagacctca gagataagat cgggccggcg ctaaccagaa ctcgctcgcc gagcccatcc   540
ggagcctttt tttcccgttt tcattccctt tctcccaacc ccctctccc ttttggtgat    600 tcgtgattct tccctttgt ttaacaccgt ccatatggac accgcccgc cggggccgtc    660 cgacgcaccg tcctacccgc agccgaggcc ctgcccctat caaccgccgc ccgcctacga   720
gcgtctgggc gcgcaggcgc cgctgtcccg ggtcaccctc ttcgacgcc gcgccgtctg    780 gttcgtcacc ggctatcccg aggcgcgtca gctcctcgcg gacccacgga tatccgccga   840
ccgtgaacgc ccggagttcc cgatcaccgc gccccgtctg cgggccgagg tctcccggcg    900
gttcatcctc ctcagcatgg acgcgcccgt ccacggcgag taccggcggc tgctcaaccc    960
ggacttcagc cgcaaacgga tcgcgagcct gcggcctgtc gtccagtccg tcgtggacga   1020
ccatctggac cggatgctgg agcaggggcc gcccgccgac ctcctgcgcg acttcgcgct   1080
gcccgtgccg tcccgggtga tctccgaact gctggggctg ccccggagg acacggagct   1140 cttccagcgg ctctccggcc ggctgctgcg ggccggcagc gccgacgacg cccaggaggc   1200
cgcccgcgaa ctcggcgact acctcggcgc cctgaccgcc cggccgcccg aaggccccgg   1260
tcccgggctg atcgcccggc tcgcccatga cgaggtcgcc acggggcggc tcagccacgc   1320
cgacctggta cggatcgccc tcgtcatcct gctcgccggg cacgagacca cggcgtccac   1380
catcacgctg ggcaccgtca ccctgctcga ccacccgag cagctcgccc gtatgcggtc    1440
cgatccggcc accgtgccgg gggcggtgga ggagatcctg cgctgtgtcg cggtcaccga   1500
tctcgcgggg gtgagggtcg ccaccgccga catcccggtc gccgggcaga tcattcgcgc   1560
cggtgaaggc gttctgctgt ccagcacgat ggccaaccgg gaccggcgcg tccacacaga   1620
cccggacacc ttcgacatcg accgcaccgg acgccaccat ctgtccttcg gctacggcat   1680
ccaccagtgc ctcggccaga gcctggcccg gatggagctg gagatcgcgt tctcggccct   1740
cttcacccgt atccccaccc tgcggctggc cgttcccgtc gaccggctgc ccaccaggcc   1800
gccgagcagc ggcgccatcc agggtttcga cgagctgccg gtgacctggt ctagataaat   1860
gcataaattt tggaatcccg cgcgctccaa tatacctacc gctacgattg aggatgcctg   1920
```

| | |
|---|---|
| ctgattcttg gtgttctgca cctgaattgg tcggcgaggt cctcatttga tgtattatct | 1980 |
| tttcaattta gctcgaaacg ttgaattcaa gttatagcaa tagacatttt ttcttttgtg | 2040 |
| atcataacgt ggacattcat tgccaagttt gtacaaaaaa gcagtcccc | 2089 |

<210> SEQ ID NO 105
<211> LENGTH: 1560
<212> TYPE: DNA
<213> ORGANISM: Artificial Sequence
<220> FEATURE:
<223> OTHER INFORMATION: Synthetic DNA

<400> SEQUENCE: 105

| | |
|---|---|
| ggggacagct ttcttgtaca aagtggggga attccacgaa caaaatacgg attcctcggg | 60 |
| cacctttag ggatcggggt gaagttattc tatacctagg tagctttcat agataatata | 120 |
| gctgttagct gtaataggtg tttcttgtat gtgatcatga agaacttcgc agtgcaaagt | 180 |
| catgatatag ttataaaagt cccctcataa ttccgttgaa gactcccttg acagctccct | 240 |
| ggacagctcc caagacctca aaacgaacgg catcgggcta tcacggggaa ggtcgggaat | 300 |
| accagcagga ttagccatac ataaagaggt tatattagat catctcatct ctcttctttt | 360 |
| tctcttttttt cttgaaatca cactgacctc actccagttc cactaaatct ccaccaccgg | 420 |
| tgagtctacc ttgtctctcc ttcaccgatg acgcttgccc ctctaccttt tgcccctcct | 480 |
| ccttatttaa ctctgcccgc tttcagctcc cggtaaagga gcttggtttc actgcattta | 540 |
| actactttac cattggatct gaccttcttt ccttcttctt tctcctacag atttatacga | 600 |
| accaatttat ttgtaccacc gtcaaaatga gctcagatac ccaccccggt acccagtccc | 660 |
| agtccctgtc cccgtcccag tccccgtcct cgttctcatc ccagccgcag ccgcagcccg | 720 |
| ccgccggcgt ctccgccggt gccggcgccg agcgctcctt cctcttcgtc ctcggcagct | 780 |
| cgcgcgccga cggcaacacc gagatcctgg cccgtgccgc cgccgcgcaa cttcccgccg | 840 |
| gtgtacgaca ggagtgggtg gatctgcggg agctggatct gcccgacttc caggacggcc | 900 |
| ggcacgagaa cggctcctgg ccggtgggcg aagccgagcg gaaactgcgc gaactgacac | 960 |
| tggcggccac cgatgtcgtc ctcgtcaccc cgctgtactg gtacacggtc tccgcgcaga | 1020 |
| tgaagcgcta tctcgactac tggtcgggct gggcgcgcga ccgtgagctc ggattccagc | 1080 |
| ggcagatggc gggccgcacc ctgtggggtg tcaccgtcat ggccgaacgt gaggagagca | 1140 |
| tcgccgacgg gctcctcatc accctcaaca actcggcggg atatctccgg atgcgcttcg | 1200 |
| gcggcgtcct gctgggcaat ggctcccggc ccggacaggt ccgcgacgac gagcgggcgg | 1260 |
| cggtccgcgc caagaccttc ttcgcccagg aggcaccgct cgcgcagtac cccgggaccg | 1320 |
| gggagtaaaa aatgttgata tctgtgtgat gtcgcatctt tgattccctt tttttgcccc | 1380 |
| ttctgattac cctcatactc tcttcatgcg gccggaaaag cgttgggcgt gcctggggat | 1440 |
| gtgggcgtcc aggttgtatg tagcgttgta ttctgacacg ctgtaatgaa tgtctatatc | 1500 |
| acggtcctta tgaccgctct gaaatatggg gccccaactt tattatacaa agttgtcccc | 1560 |

<210> SEQ ID NO 106
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 106

| | |
|---|---|
| ccttcgccga ctgagtggag aacatcaagt cccagctccc tgattttg | 48 |

<210> SEQ ID NO 107
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 107
tcgctctagc ggtgcataac actaggttga cgcgatccta cgctgatttg tgctatc      57

<210> SEQ ID NO 108
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 108
atggccagca taaccacaca aacgataaca cag                                33

<210> SEQ ID NO 109
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 109
ccttcgccga ctgactgttg ggcccttgca gtcgatcttt gag                     43

<210> SEQ ID NO 110
<211> LENGTH: 756
<212> TYPE: DNA
<213> ORGANISM: Penicillium chrysogenum
<220> FEATURE:
<221> NAME/KEY: misc_feature
<223> OTHER INFORMATION: relevant 756 bases of the pcbC promoter - Fig.
      1A

<400> SEQUENCE: 110
tgcatgttgc atcgggaaat cccaccacag ggacagccaa gcggccccgc gacttggcag    60
tgggcaaact acgcccgatt ctggtgccaa gaaccgagaa gaatgagaca gacccacgtt   120
gcactctaac cggatgctat cgacttacgg tggctgaaga ttcaacacgc tgcaacgaga   180
gccaaggtgg tccggacatt ttctacgtgc cggtttacct tggaacatcg ccgtcgttga   240
gtgcacgttg cctactctct cgtggcttgg ctgggcccac gagcccgatt gactcgacgg   300
tgttacttgg gtatctatgg ccccgttttc tggcacggta atgataagta cttactagtc   360
ttcgagcggg ggagtgttgc tctgcccgag catcaacgat tggcctgatc gcaccgtctg   420
caaatgccac ggtgcggacc gactgaaatc tcagaccacc aaagaccctc cgacttcgag   480
ttacggttac taattttaca ctggctccag cggccccatc cagtaagcat ctgggctgca   540
agcgtataat gtctccaggt tgtctcagca taaacacccc gccccgctc aggcacacag    600 gaagagagct caggtcgttt ccattgcgtc catactcttc actcattgtc atctgcagga   660
gaacttcccc tgtcccttg ccaagccctc tcttcgtcgt tgtccacgcc ttcaagtttt    720
caccattatt tttctagaca ccatggcttc caccccc                            756

<210> SEQ ID NO 111
<211> LENGTH: 750
<212> TYPE: DNA

```
<213> ORGANISM: artificial sequence
<220> FEATURE:
<223> OTHER INFORMATION: the relevant 756 bases of the Penicillium
      chrysogenum pcbC promoter with bases replaced as shown in Fig. 1A

<400> SEQUENCE: 111
catatgttgc atcgggaaat cccaccacag ggacagccaa gcggccccgc gacttggcag    60
tgggcaaact acgcccgatt ctggtgccaa gaaccgagaa gaatgagaca gacccacgtt   120
gcactctaac cggatgctat cgacttacgg tggctgaaga ttcaacacgc tgcaacgaga   180
gccaaggtgg tccggacatt ttctacgtgc cggtttacct tggaacatcg ccgtcgttga   240
gtgcacgttg cctactctct cgtggcttgg ctgggcccac gagcccgatt gactcgacgg   300
tgttacttgg gtatctatgg ccccgttttc tggcacggta atgataagta cttactagtc   360
ttcgagaatt cgagtgttgc tctgcccgag catcaacgat tggcctgatc gcaccgtctg   420
caaatgccac ggtgcggacc gactgaaatc tcagaccacc aaagaccctc cgacttcgag   480
ttacggttac taattttaca ctggctccag cggccccatc cagtaagcat ctgggctgca   540
agcgtataat gtctccaggt tgtctcagca taaacacaat tgtcaggcac acaggaagag   600
agctcaggtc gtttccattg cgtccatact cttcactcat tgtcatctgc aggagaactt   660
cccctgtccc tttgccaagc cctctcttcg tcgttgtcca cgccttcaag ttttcaccat   720 tattttcta gttaacatga tatcgatgcc                                    750

<210> SEQ ID NO 112
<211> LENGTH: 100
<212> TYPE: DNA
<213> ORGANISM: artificial sequence
<220> FEATURE:
<223> OTHER INFORMATION: the 3' part of the A. nidulans gpdA promoter
      with the CAT nucleotides inserted in front of the ATG to obtain a
      NdeI site - Fig 2A

<400> SEQUENCE: 112
ttgtcatctg caggagaact tcccctgtcc ctttgccaag ccctctcttc gtcgttgtcc    60
acgccttcaa gttttcacca ttattttcct agaccatatg                        100

<210> SEQ ID NO 113
<211> LENGTH: 100
<212> TYPE: DNA
<213> ORGANISM: Bacillus subtilis
<220> FEATURE:
<221> NAME/KEY: misc_feature
<223> OTHER INFORMATION: the essential part of the B. subtilis PE4
      promoter with the bacterial consensus elements (underlined in Fig.
      2B and Fig. 3A)

<400> SEQUENCE: 113
atccacgctg tgtaaaaatt ttacaaaaag gtattgactt tccctacagg gtgtgtaata    60
atttaattac agctcgagaa ttaaaggagg gtttcatatg                        100

<210> SEQ ID NO 114
<211> LENGTH: 97
<212> TYPE: DNA
<213> ORGANISM: artificial sequence
<220> FEATURE:
<223> OTHER INFORMATION: the 3' part of the P. chrysogenum pcbC Delta
      creAIII promoter with the CAT nucleotides inserted in front of the
      ATG to obtain a NdeI site - Fig. 2C

<400> SEQUENCE: 114
cttcccatcc cttattcctt tgaacctttc agttcgagct ttcccacttc atcgcagctt    60
```
gactaacagc taccccgctt gagcagacat ccatatg         97

<210> SEQ ID NO 115
<211> LENGTH: 85
<212> TYPE: DNA
<213> ORGANISM: Penicillium chrysogenum
<220> FEATURE:
<221> NAME/KEY: misc_feature
<223> OTHER INFORMATION: the relevant part of the PpcbC wild type
      promoter (WT) - Fig. 3B WT (with the bacterial elements included
      underlined in the figure)

<400> SEQUENCE: 115
agaacttccc ctgtcccttt gccaagccct ctcttcgtcg ttgtccacgc cttcaagttt         60
tcaccattat ttttctagac atatg         85

<210> SEQ ID NO 116
<211> LENGTH: 105
<212> TYPE: DNA
<213> ORGANISM: artificial sequence
<220> FEATURE:
<223> OTHER INFORMATION: the relevant part of the P. chrysogenum PpcbC
      promoter variant (INS) (with the bacterial elements included
      underlined and all modifications with respect to the WT sequence
      in capitals in Fig. 3B INS)

<400> SEQUENCE: 116
agaaaacttc ccctgtccct tgccaaaaa gccctctttg acttcgtcgt tgtccacgcc         60
tataattcaa gttttcacca ttatttttct ggaggagacc atatg         105

<210> SEQ ID NO 117
<211> LENGTH: 89
<212> TYPE: DNA
<213> ORGANISM: artificial sequence
<220> FEATURE:
<223> OTHER INFORMATION: the relevant part of the P. chrysogenum PpcbC
      promoter variant (EXC) (with the bacterial elements included
      underlined and all modifications with respect to the WT sequence
      in capitals - Fig. 3B EXC)

<400> SEQUENCE: 117
agaaaaactt ccctgtccc tttgactagc cctctcttcg ttgttataat cgccttcaag         60
ttttcaccat tattggagga gaccatatg         89

<210> SEQ ID NO 118
<211> LENGTH: 84
<212> TYPE: DNA
<213> ORGANISM: Aspergillus nidulans
<220> FEATURE:
<221> NAME/KEY: misc_feature
<223> OTHER INFORMATION: the relevant part of the PgpdA wild type (WT) -
      Fig. 3C WT

<400> SEQUENCE: 118
attcctttga acctttcagt tcgagctttc ccacttcatc gcagcttgac taacagctac         60
cccgcttgag cagacatcca tatg         84

<210> SEQ ID NO 119
<211> LENGTH: 101
<212> TYPE: DNA
<213> ORGANISM: artificial sequence
<220> FEATURE:
<223> OTHER INFORMATION: the relevant part of the A. nidulans PgpdA
      promoter variant (INS) (with the bacterial elements included
      underlined and all modifications with respect to the WT sequence in capitals in Fig. 3C INS)

<400> SEQUENCE: 119
attcctttga aaaacctttc aaaaagttcg agttgactttt cccacttcat cgcagcataa    60
tttgactaac agctaccccg cttgaggagg acatccatat g                         101

<210> SEQ ID NO 120
<211> LENGTH: 97
<212> TYPE: DNA
<213> ORGANISM: artificial sequence
<220> FEATURE:
<223> OTHER INFORMATION: the relevant part of the A. nidulans PgpdA
      promoter variant (EXC) (with the bacterial elements included
      underlined and all modifications with respect to the WT sequence
      in capitals in Fig. 3C EXC)

<400> SEQUENCE: 120
cttcccatcc cttattccta aaaccttttt tgactgagct ttcccacttt gtcataattt    60
gactaacagc tacccgctt gaggaggcat ccatatg                              97

<210> SEQ ID NO 121
<211> LENGTH: 87
<212> TYPE: DNA
<213> ORGANISM: Penicillium chrysogenum
<220> FEATURE:
<221> NAME/KEY: misc_feature
<223> OTHER INFORMATION: promoter of Pc12g14840 wt = wild type (with
      essential elements underlined in Fig. 5A)

<400> SEQUENCE: 121
ctcttggaaa gtcttggaaa ttgactcttt tttgcctcct tttacaatct acccctttta    60
atctttgcga ctcgtttctt caccatg                                        87

<210> SEQ ID NO 122
<211> LENGTH: 87
<212> TYPE: DNA
<213> ORGANISM: artificial sequence
<220> FEATURE:
<223> OTHER INFORMATION: variant promoter of P. chrysogenum Pc12g14840
      with CAT introduced to create a NdeI site (CD1 in Fig. 5A)

<400> SEQUENCE: 122
ctcttggaaa gtcttggaaa ttgactcttt tttgcctcct tttacaatct acccctttta    60
atctttgcga ctcgtttctt ccatatg                                        87

<210> SEQ ID NO 123
<211> LENGTH: 87
<212> TYPE: DNA
<213> ORGANISM: artificial sequence
<220> FEATURE:
<223> OTHER INFORMATION: variant promoter of P. chrysogenum Pc12g14840
      with additionally a ribosome binding site introduced (CD2,
      ribosome binding site underlined and basepairs introduced in
      capitals in Fig. 5A)

<400> SEQUENCE: 123
ctcttggaaa gtcttggaaa ttgactcttt tttgcctcct tttacaatct acccatttta    60
atctttgcga ctggaggctt ccatatg                                        87

I claim:

1. An expression cassette comprising a gene-of-interest and a polynucleotide control sequence which directs the expression of polypeptides in at least three of the following groups of host cells: algae, fungi, yeasts, gram-positive bacteria, gram-negative bacteria, wherein the polynucleotide control sequence comprises a polynucleotide sequence of the general formula T-T-G-A-C—W-N(o)-$Y_1$-A-$Y_2$-A-A-T-$H_1$-$H_2$-N(p)-$S_1$-$S_2$-W-$K_1$-$K_2$-N(q)-$H_3$-$M_1$-$M_2$-$H_4$-A-T-G, (formula I) wherein the polynucleotide sequence is selected from any one of SEQ ID NOS: 1 to 51, wherein
   N is any of the nucleotides A, C, G and T, and N(o) is 16, 17 or 18 nucleotides long;
   N(p) is 22 nucleotides long;
   N(q) is 2, 3, 4, 5 or 6 nucleotides long; and
   each individual N in N(o), N(p), and N(q) are the same or different;
   W is any of the nucleotides A and T;
   Y is any of the nucleotides C and T, and $Y_1$ and $Y_2$ are the same or different;
   H is any of the nucleotides A, C, and T and $H_1$, $H_2$, $H_3$ and $H_4$ are the same or different;
   S is any of the nucleotides G and C, and $S_1$ and $S_2$ are the same or different;
   K is any of the nucleotides G and T, and $K_1$ and $K_2$ are the same or different;
   M is any of the nucleotides A and C, and $M_1$ and $M_2$ are the same or different;
   the AG-content of N(o) is below 50%;
   the A-content of N(o) is below 35%;
   the AG-content within each stretch of 6 nucleotides in N(o) is below 66%;
   the AG-content of N(p) is below 60%;
   the AG-content within each stretch of 6 nucleotides in N(p) is below 83%;
   N(o) and N(p) do not contain two consecutive G's; and
   the G-content of N(q) is below 50%,
   wherein the polynucleotide control sequence is either heterologous to the host cell or to the gene-of-interest coding for the polypeptide.

2. The expression cassette according to claim 1, wherein N(o) is 17 nucleotides long; N(p) is 22 nucleotides long; and N(q) is 3 or 4 nucleotides long.

3. The expression cassette according to claim 1, wherein the polynucleotide control sequence is selected from the group consisting of SEQ ID NO. 46 to 51.

4. The expression cassette according to claim 1 which directs the expression of polypeptides in at least four of the following genera: *Escherichia, Streptomyces, Bacillus, Gluconobacter, Pseudomonas, Clostridium, Saccharomyces, Kluyveromyces, Pichia, Penicillium, Aspergillus, Mortierella, Chrysosporium, Acremonium, Trichoderma.*

5. A vector comprising an expression cassette, wherein the expression cassette comprises a polynucleotide sequence and a gene-of-interest, wherein the polynucleotide control sequence comprises a polynucleotide sequence of the general formula
   T-T-G-A-C-W-N(o)-$Y_1$-A-$Y_2$-A-A-T-$H_1$-$H_2$-N(p)-$S_1$-$S_2$-W-$K_1$-$K_2$-N(q)-$H_3$-$M_1$-$M_2$-$H_4$-A-T-G, (formula I) wherein the polynucleotide sequence is selected from any one of SEQ ID NOS: 1 to 51, wherein
   N is any of the nucleotides A, C, G and T, and N(o) is 16, 17 or 18 nucleotides long;
   N(p) is 22 nucleotides long;
   N(q) is 2, 3, 4, 5 or 6 nucleotides long; and
   each individual N in N(o), N(p), and N(q) are the same or different;
   W is any of the nucleotides A and T;
   Y is any of the nucleotides C and T, and $Y_1$ and $Y_2$ are the same or different;
   H is any of the nucleotides A, C, and T and $H_1$, $H_2$, $H_3$ and $H_4$ are the same or different;
   S is any of the nucleotides G and C, and $S_1$ and $S_2$ are the same or different;
   K is any of the nucleotides G and T, and $K_1$ and $K_2$ are the same or different;
   M is any of the nucleotides A and C, and $M_1$ and $M_2$ are the same or different;
   the AG-content of N(o) is below 50%;
   the A-content of N(o) is below 35%;
   the AG-content within each stretch of 6 nucleotides in N(o) is below 66%;
   the AG-content of N(p) is below 60%;
   the AG-content within each stretch of 6 nucleotides in N(p) is below 83%;
   N(o) and N(p) do not contain two consecutive G's; and
   the G-content of N(q) is below 50%,
   wherein the polynucleotide control sequence directs expression of the gene-of-interest in at least three of the following groups of host cells: algae, fungi, yeast, gram-positive bacteria, gram-negative bacteria, wherein the polynucleotide control sequence is either heterologous to the host cell or to the gene-of-interest coding for the polypeptide.

6. A host cell comprising the vector according to claim 5.

7. A method of producing a polypeptide, a primary or secondary metabolite, an antibody or a pharmaceutical with a host cell according to claim 6.

8. A method according to claim 7, wherein the host cell is a cloning host, and wherein the polypeptide, primary or secondary metabolite, antibody or pharmaceutical is produced in a production host, which method comprises using the same polynucleotide control sequence in both cloning host and production host.

9. The method according to claim 8, wherein the polynucleotide control sequence is a control sequence.

10. The method according to claim 8, wherein the production host is of a different species than the cloning host.

11. A method for cloning a polynucleotide sequence comprising:
    (a) cloning a polynucleotide sequence in front of a selectable marker gene on a vector according to the invention;
    (b) transfecting a first species with the vector from step (a);
    (c) obtaining clones after selection for active transcription of the selectable marker gene;
    (d) isolating DNA from these clones;
    (e) transfecting another species with the isolated DNA, wherein steps (c) to (e) are repeated minimally 2 times;
    wherein the polynucleotide sequence is of the general formula
    T-T-G-A-C-W-N(o)-$Y_1$-A-$Y_2$-A-A-T-$H_1$-$H_2$-N(p)-$S_1$-$S_2$-W-$K_1$-$K_2$-N(q)-$H_3$-$M_1$-$M_2$-$H_4$-A-T-G, (formula I) wherein the polynucleotide sequence is selected from any one of SEQ ID NOS: 1 to 51, wherein
    N is any of the nucleotides A, C, G and T, and N(o) is 16, 17 or 18 nucleotides long;
    N(p) is 22 nucleotides long;
    N(q) is 2, 3, 4, 5 or 6 nucleotides long; and
    each individual N in N(o), N(p), and N(q) are the same or different;
    W is any of the nucleotides A and T;

Y is any of the nucleotides C and T, and $Y_1$ and $Y_2$ are the same or different;

H is any of the nucleotides A, C, and T and $H_1$, $H_2$, $H_3$ and $H_4$ are the same or different;

S is any of the nucleotides G and C, and $S_1$ and $S_2$ are the same or different;

K is any of the nucleotides G and T, and $K_1$ and $K_2$ are the same or different;

M is any of the nucleotides A and C, and $M_1$ and $M_2$ are the same or different;

the AG-content of N(o) is below 50%;

the A-content of N(o) is below 35%;

the AG-content within each stretch of 6 nucleotides in N(o) is below 66%;

the AG-content of N(p) is below 60%;

the AG-content within each stretch of 6 nucleotides in N(p) is below 83%;

N(o) and N(p) do not contain two consecutive G's; and the G-content of N(q) is below 50%.

12. A molecular biology kit comprising at least one reagent and a polynucleotide control sequence according to claim 1.

13. The expression cassette according to claim 1, wherein the polynucleotide control sequence is selected from the group consisting of SEQ ID NO. 46.

14. The expression cassette according to claim 1, wherein the polynucleotide control sequence is selected from the group consisting of SEQ ID NO. 47.

15. The expression cassette according to claim 1, wherein the polynucleotide control sequence is selected from the group consisting of SEQ ID NO. 48.

16. The expression cassette according to claim 1, wherein the polynucleotide control sequence is selected from the group consisting of SEQ ID NO. 49.

17. The expression cassette according to claim 1, wherein the polynucleotide control sequence is selected from the group consisting of SEQ ID NO. 50.

18. The expression cassette according to claim 1, wherein the polynucleotide control sequence is selected from the group consisting of SEQ ID NO. 51.

* * * * *